US012724982B1

(12) United States Patent
Subramaniam

(10) Patent No.: US 12,724,982 B1
(45) Date of Patent: Sep. 1, 2026

(54) TRACKING CLINICAL OUTCOME ASSESSMENTS IN PUBLICATIONS

(71) Applicant: ICON Clinical Research Limited, Dublin (IE)

(72) Inventor: Haribaskar Subramaniam, Dublin (IE)

(73) Assignee: ICON Clinical Research Limited, Dublin (IE)

(*) Notice: Subject to any disclaimer, the term of this patent is extended or adjusted under 35 U.S.C. 154(b) by 0 days.

(21) Appl. No.: 18/963,917

(22) Filed: Nov. 29, 2024

(51) Int. Cl.

| | |
|---|---|
| ***G16H 10/20*** | (2018.01) |
| ***G06F 40/205*** | (2020.01) |
| ***G06F 40/284*** | (2020.01) |
| ***G06F 40/30*** | (2020.01) |
| ***G06F 40/40*** | (2020.01) |
| ***G06N 3/045*** | (2023.01) |

(Continued)

(52) U.S. Cl.
CPC ............ *G06F 40/40* (2020.01); *G06F 40/205* (2020.01); *G06F 40/284* (2020.01); *G06F 40/30* (2020.01); *G06N 3/045* (2023.01); *G06N 3/0985* (2023.01); *G06N 20/20* (2019.01); *G16H 10/20* (2018.01)

(58) Field of Classification Search
CPC ...... G16H 10/20; G06N 20/20; G06N 3/0985; G06N 3/045; G06F 40/205; G06F 40/117; G06F 40/284; G06F 40/40; G06F 40/30
See application file for complete search history.

(56) References Cited

U.S. PATENT DOCUMENTS 10,810,512 B1 * 10/2020 Wubbels ................ G06N 20/20
11,056,216 B2 7/2021 Jovic et al.

(Continued)

FOREIGN PATENT DOCUMENTS

CN 116303980 B 6/2023
CN 116756579 B 9/2023

(Continued)

OTHER PUBLICATIONS

Pettit et al., "Artificial intelligence, machine learning, and deep learning for clinical outcome prediction," Emerging Topics in Life Sciences (2021) 5 729-745; https://doi.org/10.1042/ETLS20210246. (Year: 2021).*

(Continued)

*Primary Examiner* — Jonathon A. Szumny
(74) *Attorney, Agent, or Firm* — Davé Law Group, LLC; Raj S. Davé

(57) ABSTRACT

According to an embodiment, disclosed is a system comprising a processor storing instructions in a non-transitory memory that, when executed, cause the processor to, acquire pre-processed input data from one or more data sources; train, a first machine learning model with the pre-processed input data, wherein the first machine learning model is configured to, analyze the pre-processed input data for availability of clinical outcome assessment; extract one or more features from the pre-processed input data; predict a dataset from the pre-processed input data based on the features and a predefined threshold value, wherein the dataset has availability of the clinical outcome assessment; wherein the predicted dataset is configured to train a second machine learning model; and wherein the second machine learning model is configured to generate content related to clinical outcome assessment names.

19 Claims, 16 Drawing Sheets

(51) Int. Cl.

| | |
|---|---|
| ***G06N 3/0985*** | (2023.01) |
| ***G06N 20/20*** | (2019.01) |

(56) References Cited

U.S. PATENT DOCUMENTS

| | | | | |
|---|---|---|---|---|
| 11,074,062 | B1 * | 7/2021 | Hosic | G06F 8/65 |
| 11,621,085 | B1 | 4/2023 | Gottula et al. | |
| 11,862,345 | B2 | 1/2024 | Ghazaleh et al. | |
| 11,915,419 | B1 * | 2/2024 | Behrooz | G16H 50/20 |
| 12,200,167 | B1 * | 1/2025 | Mecca | H04M 3/42068 |
| 12,259,864 | B1 * | 3/2025 | Aravamudan | G16H 50/70 |
| 2014/0257047 | A1 * | 9/2014 | Sillay | H04L 63/10 600/595 |
| 2018/0247153 | A1 * | 8/2018 | Ganapati | G06F 18/285 |
| 2019/0077409 | A1 * | 3/2019 | Zandi | G06F 3/013 |
| 2019/0095805 | A1 * | 3/2019 | Tristan | G06N 5/045 |
| 2020/0394361 | A1 * | 12/2020 | Parikh | H04L 67/08 |
| 2021/0295956 | A1 | 9/2021 | Adhikari | |
| 2021/0327540 | A1 * | 10/2021 | Schobel | G16H 50/20 |
| 2021/0342652 | A1 * | 11/2021 | Glassman | G06F 18/2113 |
| 2022/0237373 | A1 * | 7/2022 | Singh Bawa | G06N 20/00 |
| 2022/0344008 | A1 * | 10/2022 | Limsopatham | G06F 40/137 |
| 2023/0022845 | A1 * | 1/2023 | Meng | G06F 40/279 |
| 2023/0298707 | A1 * | 9/2023 | Gray | G06F 40/295 705/2 |
| 2023/0402180 | A1 * | 12/2023 | Molero Leon | G06N 3/0455 |
| 2024/0105289 | A1 * | 3/2024 | Khan | G16H 15/00 |
| 2024/0126924 | A1 * | 4/2024 | Pabolu | G06F 21/6254 |
| 2024/0266009 | A1 * | 8/2024 | Vold | G06F 40/295 |
| 2024/0320445 | A1 * | 9/2024 | Mallick | G06F 40/30 |
| 2024/0331445 | A1 * | 10/2024 | Sekar | G06V 10/7715 |
| 2024/0363247 | A1 * | 10/2024 | Attia | G16H 50/30 |
| 2024/0411732 | A1 * | 12/2024 | Singh | G06N 3/048 |
| 2025/0062020 | A1 * | 2/2025 | Gordon | G16H 30/40 |
| 2025/0166202 | A1 * | 5/2025 | Krishnan | G06T 7/0016 |
| 2025/0209694 | A1 * | 6/2025 | Hirokawa | G06N 20/20 |
| 2025/0238715 | A1 * | 7/2025 | Danke | G06N 20/00 |
| 2025/0330325 | A1 * | 10/2025 | Fortkort | H04L 9/3231 |

FOREIGN PATENT DOCUMENTS

| | | | | | |
|---|---|---|---|---|---|
| CN | 117577350 | B | | 2/2024 | |
| CN | 117952121 | A | | 4/2024 | |
| EP | 4352745 | A1 | | 4/2024 | |
| KR | 20160068868 | A | * | 6/2016 | G06F 19/36 |
| WO | WO-2022029428 | A1 | * | 2/2022 | G06N 5/02 |
| WO | WO-2024039466 | A1 | * | 2/2024 | G16B 40/20 |
| WO | WO-2024059094 | A1 | * | 3/2024 | |
| WO | WO-2024207041 | A1 | * | 10/2024 | G06N 20/00 |

OTHER PUBLICATIONS

Prasad et al., "Deep learning for the prediction of clinical outcomes in internet-delivered CBT for depression and anxiety," PLoS One 18(11): e0272685. https://doi.org/10.1371/journal.pone.0272685. (Year: 2023).*

Abdullah et al., "Evaluating the Performance of Clinical data using Machine learning Approach—An Ensemble Model," 2024 Second International Conference on Networks, Multimedia and Information Technology (NMITCON); DOI: 10.1109/NMITCON62075.2024.10699100. (Year: 2024).*

Shamout et al., "Machine Learning for Clinical Outcome Prediction," IEEE Reviews in Biomedical Engineering, vol. 14, 2021; Digital Object Identifier 10.1109/RBME.2020.3007816. (Year: 2021).*

Understanding Clinical Trial Reports: Extracting Medical Entities and Their Relation dated Jan. 7, 2022, 10 Pages.

* cited by examiner

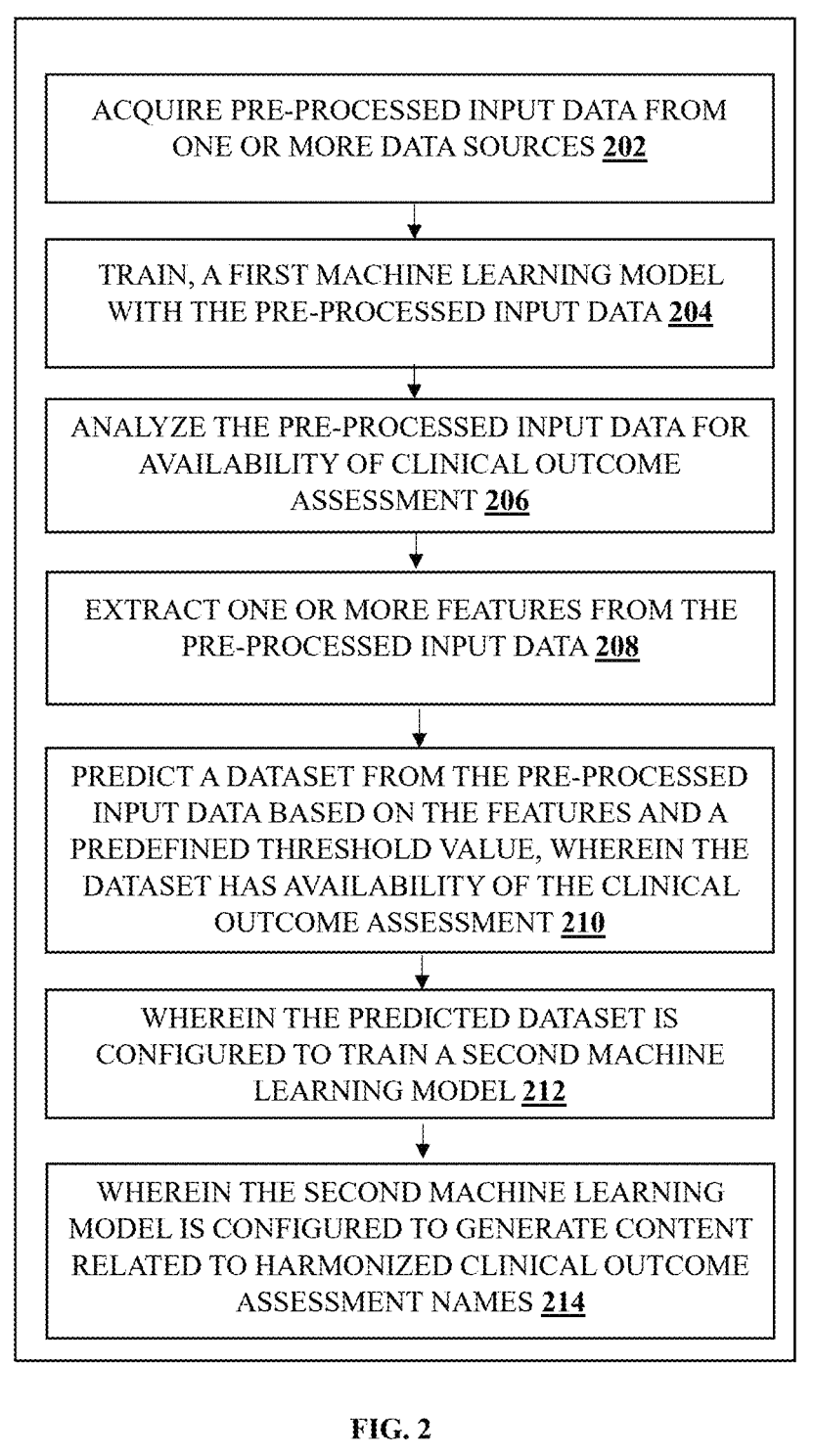

ACQUIRE PRE-PROCESSED INPUT DATA FROM ONE OR MORE DATA SOURCES 202

TRAIN, A FIRST MACHINE LEARNING MODEL WITH THE PRE-PROCESSED INPUT DATA 204

ANALYZE THE PRE-PROCESSED INPUT DATA FOR AVAILABILITY OF CLINICAL OUTCOME ASSESSMENT 206

EXTRACT ONE OR MORE FEATURES FROM THE PRE-PROCESSED INPUT DATA 208

PREDICT A DATASET FROM THE PRE-PROCESSED INPUT DATA BASED ON THE FEATURES AND A PREDEFINED THRESHOLD VALUE, WHEREIN THE DATASET HAS AVAILABILITY OF THE CLINICAL OUTCOME ASSESSMENT 210

WHEREIN THE PREDICTED DATASET IS CONFIGURED TO TRAIN A SECOND MACHINE LEARNING MODEL 212

WHEREIN THE SECOND MACHINE LEARNING MODEL IS CONFIGURED TO GENERATE CONTENT RELATED TO HARMONIZED CLINICAL OUTCOME ASSESSMENT NAMES 214

FIG. 2

Accuracy: 0.9435

Classification Report

| | precision | recall | f1-score | support |
|---|---|---|---|---|
| 0 | 0.93 | 0.96 | 0.94 | 1000 |
| 1 | 0.96 | 0.93 | 0.94 | 1000 |
| accuracy | | | 0.94 | 2000 |
| macro avg | 0.94 | 0.94 | 0.94 | 2000 |
| weighted avg | 0.94 | 0.94 | 0.94 | 2000 |

Accuracy: 0.9432739059967585

Classification Report

| | precision | recall | f1-score | support |
|---|---|---|---|---|
| 0 | 0.92 | 0.97 | 0.94 | 601 |
| 1 | 0.97 | 0.92 | 0.94 | 633 |
| accuracy | | | 0.94 | 1234 |
| macro avg | 0.94 | 0.94 | 0.94 | 1234 |
| weighted avg | 0.94 | 0.94 | 0.94 | 1234 |

Accuracy: 0.9805

Classification Report

| | precision | recall | f1-score | support |
|---|---|---|---|---|
| 0 | 0.98 | 0.98 | 0.98 | 1000 |
| 1 | 0.98 | 0.98 | 0.98 | 1000 |
| accuracy | | | 0.98 | 2000 |
| macro avg | 0.98 | 0.98 | 0.98 | 2000 |
| weighted avg | 0.98 | 0.98 | 0.98 | 2000 |

Accuracy: 0.9789303079416531

Classification Report

| | precision | recall | f1-score | support |
|---|---|---|---|---|
| 0 | 0.98 | 0.98 | 0.98 | 601 |
| 1 | 0.98 | 0.98 | 0.98 | 633 |
| accuracy | | | 0.98 | 1234 |
| macro avg | 0.98 | 0.98 | 0.98 | 1234 |
| weighted avg | 0.98 | 0.98 | 0.98 | 1234 |

```
Accuracy:  0.9774273345701917

Classification Report
=======================================================

              precision    recall  f1-score   support

           0       0.98      0.98      0.98      1601
           1       0.98      0.98      0.98      1633

    accuracy                           0.98      3234
   macro avg       0.98      0.98      0.98      3234
weighted avg       0.98      0.98      0.98      3234
```

ANN/ML MODEL

X (INPUT)

Y (OUTPUT)

ERROR SIGNAL

FEEDBACK

REINFORCEMENT SIGNAL

TRACKING CLINICAL OUTCOME ASSESSMENTS IN PUBLICATIONS

FIELD OF THE INVENTION

The present disclosure relates to systems and methods of data processing. More specifically, the present disclosure relates to systems and methods of data curation augmented by machine learning algorithms and artificial Intelligence (AI) models.

BACKGROUND

"Currently, Randomized Controlled Trials (RCTs) pertaining to specific clinical questions are manually identified and synthesized in systematic reviews that in turn inform guidelines, health policies, and medical decision-making. Such reviews are critically important, but onerous to produce. Moreover, reliance on these manually compiled syntheses means that even when a systematic review relevant to a particular clinical question or topic exists, it is likely that new evidence will have been published since its compilation, rendering it out of date. Language technologies that make the primary literature more actionable by surfacing relevant evidence could expedite evidence synthesis2 and enable health practitioners to inform care using the totality of the available evidence." [Source: Understanding Clinical Trial Reports: Extracting Medical Entities and Their Relations-arXiv]

Currently, there is no technology that systematically tracks clinical trial outcomes (COAs) in clinical publications or repositories. AI capabilities used in existing databases are not specific to the COA field and do not have sufficient accuracy, recall or precision for the intended use. Therefore, data provided by current solutions still needs substantial time-consuming manual review. Due to this lack of technology, there is also no existing solution that curates all needed COA information at one place. Sponsors need to use multiple solutions to build their COA strategy, including subscribing to databases, paying for literature review software, or commissioning external consultancy services, and manually reconciling data.

Therefore, there is a need for an innovative solution to track clinical outcome assessments in clinical repositories and scientific publications.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

According to an embodiment, disclosed is a system comprising a processor storing instructions in a non-transitory memory that, when executed, cause the processor to, acquire pre-processed input data from one or more data sources; train, a first machine learning model with the pre-processed input data, wherein the first machine learning model is configured to, analyze the pre-processed input data for availability of clinical outcome assessment; extract one or more features from the pre-processed input data; predict a dataset from the pre-processed input data based on the features and a predefined threshold value, wherein the dataset has availability of the clinical outcome assessment; wherein the predicted dataset is configured to train a second machine learning model; and wherein the second machine learning model is configured to generate content related to clinical outcome assessment names.

According to an embodiment of the system, the pre-processed input data comprises at least one of structured data, semi-structured data, and unstructured data.

According to an embodiment of the system, the data sources comprise at least one of a clinical study description, a scientific publication, a research publication, a clinical investigation, and a clinical research study.

According to an embodiment of the system, the pre-processed input data from the data sources is stored in a database.

According to an embodiment of the system, the data sources comprise at least one of a textual data, a numerical data, a graphical representation, a chart, and a table.

According to an embodiment of the system, the first machine learning model is further configured to: cleanse and filter the pre-processed input data based on at least one of an input from a user, and a predefined rule.

According to an embodiment of the system, the first machine learning model is configured to perform one or more of a normalization, a standardization, and a stratification of the pre-processed input data.

According to an embodiment of the system, the system is further configured to: customize the first machine learning model by at least one of manipulating the pre-processed input data, adding, modifying, and removing at least one node of the first machine learning model, and training the first machine learning model using the manipulated pre-processed input data.

According to an embodiment of the system, the system is further configured to: enable a user to interact with a server through a user interface, provided via a device associated with the user, and (enable the user to) perform at least one of build, train, re-train, replicate, compare, and share the first machine learning model.

According to an embodiment of the system, the predefined threshold value is initially set based on at least one of outcomes of historical input data and predictions by the first machine learning model.

According to an embodiment of the system, the first machine learning model comprises at least one of a Random Forest classifier model, an XGBoost model, a Support Vector Machine (SVM) model, a Stochastic Gradient Descent model, and a Logistic Regression model.

According to an embodiment of the system, the first machine learning model further comprises a hard voting algorithm.

According to an embodiment of the system, the system is configured to display the dataset.

According to an embodiment of the system, the system is configured for tracking of the clinical outcome assessment.

According to an embodiment of the system, the first machine learning model is calibrated and selected from one or more artificial intelligence (AI) models for tracking of the clinical outcome assessment by evaluating AI model candidates against a set of performance criteria.

According to an embodiment of the system, the set of performance criteria comprise prediction accuracy, computational efficiency, and adaptability to diverse pre-processed input data.

According to an embodiment of the system, the processor is configured to stratify a feature into one of low, medium, and high relevance categories.

According to an embodiment of the system, the first machine learning model comprises a neural network comprising a non-linear activation function configured to capture a non-linear association with the pre-processed input data.

According to an embodiment of the system, the first machine learning model is configured to learn using labelled data using a supervised learning model, wherein the supervised learning model comprises logic using at least one of a decision tree, a logistic regression, a support vector machine, a k-nearest neighbors, a Naïve Bayes, a random forest, a linear regression, a polynomial regression, and a support vector machine for regression.

According to an embodiment of the system, the first machine learning model is a first self-learning model.

According to an embodiment of the system, the first machine learning model has a feedback loop, wherein an output from a previous step is fed back to the model in real-time to improve performance and accuracy of the output of a next step.

According to an embodiment of the system, the first machine learning model comprises a feedback loop, wherein the learning is further reinforced with a reward for each true positive of an output of the system.

According to an embodiment of the system, the processor is further configured to: train a second machine learning model with the dataset, wherein the second machine learning model is configured to, extract a keyword from the dataset based on regular expressions generated with predetermined rules According to an embodiment of the system, wherein the second machine learning model is a second self-learning model comprising a second feedback layer that enables the second machine learning model to learn continuously from the updated dataset.

According to an embodiment of the system, the keyword comprises a clinical outcome assessment name.

According to an embodiment of the system, the processor is further configured to assign a weight to the keyword based on a first pattern of outcomes of historical datasets.

According to an embodiment of the system, the processor is further configured to modify the weight of the keyword based on a second pattern of outcomes of training datasets.

According to an embodiment of the system, the second machine learning model is further configured to: perform word frequency analysis on the dataset to determine word frequency in the dataset; and optimize the keyword in the dataset based on the word frequency.

According to an embodiment of the system, the second machine learning model is further configured to: identify the keyword having a word frequency above a threshold; and update the keyword based on words not included in the keyword from the dataset extracted based on the regular expressions and having a higher than a threshold word frequency.

According to an embodiment of the system, the second machine learning model is further configured to: validate the keyword; and generate an indication that the keyword is validated.

According to an embodiment of the system, the processor is further configured to: perform data curation of the keyword.

According to an embodiment of the system, the data curation comprises a rule-based algorithm to reconcile and harmonize the keyword based on a second predefined threshold value.

According to an embodiment of the system, the rule-based algorithm comprises a natural language processing (NLP) algorithm.

According to an embodiment, disclosed is a method comprising, acquiring, by a processor, pre-processed input data from one or more data sources; training, by the processor, a first machine learning model with the pre-processed input data; analyzing, by the first machine learning model, the pre-processed input data for availability of clinical outcome assessment; extracting, by the first machine learning model, one or more features from the pre-processed input data; predicting, by the first machine learning model, a dataset from the pre-processed input data based on the features and a predefined threshold value, wherein the dataset has availability of the clinical outcome assessment; wherein the predicted dataset is configured to train a second machine learning model; and wherein the second machine learning model is configured to generate content related to clinical outcome assessment names.

According to an embodiment of the method, the pre-processed input data comprises at least one of structured data, semi-structured data, and unstructured data.

According to an embodiment of the method, the data sources comprise at least one of a clinical study description, a scientific publication, a research publication, a clinical investigation, and a clinical research study.

According to an embodiment of the method, the pre-processed input data from the data sources is stored in a database.

According to an embodiment of the method, the data sources comprise at least one of a textual data, a numerical data, a graphical representation, a chart, and a table.

According to an embodiment of the method, the method further comprises cleansing and filtering the pre-processed input data based on at least one of an input from a user, and a predefined rule.

According to an embodiment of the method, the method further comprises performing one or more of a normalization, a standardization, and a stratification of the pre-processed input data.

According to an embodiment of the method, the method further comprising customizing the first machine learning model by at least one of manipulating the pre-processed input data, adding, modifying, and removing at least one node of the first machine learning model, and training the first machine learning model using the manipulated pre-processed input data.

According to an embodiment of the method, the method further comprising enabling a user to interact with a server through a user interface, provided via a device associated with the user, and at least one of building, training, re-training, replicating, comparing, and sharing the first machine learning model.

According to an embodiment of the method, the predefined threshold value is initially set based on at least one of outcomes of historical input data and predicted by the first machine learning model.

According to an embodiment of the method, the first machine learning model comprises at least one of a Random Forest classifier model, an XGBoost model, a Support Vector Machine (SVM) model, a Stochastic Gradient Descent model, and a Logistic Regression model.

According to an embodiment of the method, the first machine learning model further comprises a hard voting algorithm.

According to an embodiment of the method, the method further comprises displaying the dataset.

According to an embodiment of the method, the method is configured for tracking of the clinical outcome assessment.

According to an embodiment of the method, the first machine learning model is calibrated and selected from one or more artificial intelligence (AI) models for tracking of clinical outcome assessment by evaluating AI model candidates against a set of performance criteria.

According to an embodiment of the method, the set of performance criteria comprise prediction accuracy, computational efficiency, and adaptability to diverse pre-processed input data.

According to an embodiment of the method, the method is configured for stratifying a feature into one of low, medium, and high relevance categories.

According to an embodiment of the method, the first machine learning model comprises a neural network comprising a non-linear activation function configured to capture a non-linear association with the pre-processed input data.

According to an embodiment of the method, the first machine learning model is configured to learn using labelled data using a supervised learning model, wherein the supervised learning model comprises logic using at least one of a decision tree, a logistic regression, a support vector machine, a k-nearest neighbors, a Naïve Bayes, a random forest, a linear regression, a polynomial regression, and a support vector machine for regression.

According to an embodiment of the method, the first machine learning model is a first self-learning model.

According to an embodiment of the method, the first machine learning model has a feedback loop, wherein an output from a previous step is fed back to the model in real-time to improve performance and accuracy of the output of a next step.

According to an embodiment of the method, the first machine learning model comprises a feedback loop, wherein the learning is further reinforced with a reward for each true positive of an output of the method.

According to an embodiment of the method, the method further comprising training, by the processor, a second machine learning model with the dataset; extracting, by the second machine learning model, a keyword from the dataset based on regular expressions generated with predetermined rules.

According to an embodiment of the method, wherein the second machine learning model is a second self-learning model comprising a second feedback layer that enables the second machine learning model to learn continuously from the dataset.

According to an embodiment of the method, wherein the keyword comprises a clinical outcome assessment name.

According to an embodiment of the method, the method further comprises assigning a weight to the keyword based on a first pattern of outcomes of historical datasets.

According to an embodiment of the method, the method further comprises modifying the weight of the keyword based on a second pattern of outcomes of training datasets.

According to an embodiment of the method, the method further comprises performing word frequency analysis on the dataset to determine word frequency in the dataset; and optimizing the keyword in the dataset based on the word frequency.

According to an embodiment of the method, the method further comprising identifying the keyword having a word frequency above a threshold; and updating the keyword based on words not included in the keyword from the dataset extracted based on the regular expressions and having a higher than a threshold word frequency.

According to an embodiment of the method, the method further comprises validating the keyword; and generating an indication that the keywords are validated.

According to an embodiment of the method, the method further comprises performing data curation of the keyword.

According to an embodiment of the method, the data curation comprises a rule-based algorithm to reconcile and harmonize the keyword based on a second predefined threshold value.

According to an embodiment of the method, the rule-based algorithm comprises natural language processing (NLP) algorithm.

According to an embodiment, disclosed is a non-transitory computer-readable medium having stored thereon instructions executable by a computer system to perform operations comprising acquiring, by a processor, pre-processed input data from one or more data sources; training, by the processor, a first machine learning model with the pre-processed input data; analyzing, by the first machine learning model, the pre-processed input data for availability of clinical outcome assessment; extracting, by the first machine learning model, one or more features from the pre-processed input data; predicting, by the first machine learning model, a dataset from the pre-processed input data based on the features and a predefined threshold value, wherein the dataset has availability of the clinical outcome assessment; wherein the predicted dataset is configured to train a second machine learning model; and wherein the second machine learning model is configured to generate content related to clinical outcome assessment names.

According to an embodiment of the non-transitory computer-readable medium, wherein the first machine learning model is a first self-learning model.

According to an embodiment of the non-transitory computer-readable medium, the pre-processed input data comprises at least one of structured data, semi-structured data, and unstructured data.

According to an embodiment of the non-transitory computer-readable medium, the data sources comprise at least one of a clinical study description, a scientific publication, a research publication, a clinical investigation, and a clinical research study.

According to an embodiment of the non-transitory computer-readable medium, the pre-processed input data from the data sources is stored in a database.

According to an embodiment of the non-transitory computer-readable medium, the data sources comprise at least one of a textual data, a numerical data, a graphical representation, a chart, and a table.

According to an embodiment the non-transitory computer-readable medium, further comprising cleansing and filtering the pre-processed input data based on at least one of an input from a user, and a predefined rule.

According to an embodiment the non-transitory computer-readable medium, further comprising performing one or more of a normalization, a standardization, and a stratification of the pre-processed input data.

According to an embodiment the non-transitory computer-readable medium, further comprising customizing the first machine learning model by at least one of manipulating the pre-processed input data, adding, modifying, and removing at least one node of the first machine learning model, and training the first machine learning model using the manipulated pre-processed input data.

According to an embodiment the non-transitory computer-readable medium, further comprising enabling a user to interact with a server through a user interface, provided via a device associated with the user, and at least one of building, training, re-training, replicating, comparing, and sharing the first machine learning model.

According to an embodiment of the non-transitory computer-readable medium, the predefined threshold value is initially set based on at least one of outcomes of historical input data and predicted by the first machine learning model.

According to an embodiment of the non-transitory computer-readable medium, the first machine learning model comprises at least one of a Random Forest classifier model, an XGBoost model, a Support Vector Machine (SVM) model, a Stochastic Gradient Descent model, and a Logistic Regression model.

According to an embodiment of the non-transitory computer-readable medium, the first machine learning model further comprises a hard voting algorithm.

According to an embodiment the non-transitory computer-readable medium further comprises displaying the dataset.

According to an embodiment of the non-transitory computer-readable medium, the medium and the computer system are further configured for tracking of the clinical outcome assessment.

According to an embodiment of the non-transitory computer-readable medium, the first machine learning model is calibrated and selected from one or more artificial intelligence (AI) models for tracking of clinical outcome assessment by evaluating AI model candidates against a set of performance criteria.

According to an embodiment of the non-transitory computer-readable medium, the set of performance criteria comprise prediction accuracy, computational efficiency, and adaptability to diverse pre-processed input data.

According to an embodiment of the non-transitory computer-readable medium, the medium and the computer system are further configured for stratifying a feature into one of low, medium, and high relevance categories.

According to an embodiment of the non-transitory computer-readable medium, the first machine learning model comprises a neural network comprising a non-linear activation function configured to capture a non-linear association with the pre-processed input data.

According to an embodiment of the non-transitory computer-readable medium, the first machine learning model is configured to learn using labelled data using a supervised learning model, wherein the supervised learning model comprises logic using at least one of a decision tree, a logistic regression, a support vector machine, a k-nearest neighbors, a Naïve Bayes, a random forest, a linear regression, a polynomial regression, and a support vector machine for regression.

According to an embodiment of the non-transitory computer-readable medium, the first machine learning model has a feedback loop, wherein an output from a previous step is fed back to the model in real-time to improve performance and accuracy of the output of a next step.

According to an embodiment of the non-transitory computer-readable medium, the first machine learning model comprises a feedback loop, wherein the learning is further reinforced with a reward for each true positive of an output.

According to an embodiment, the non-transitory computer-readable medium further comprising training, by the processor, a second machine learning model with the dataset; extracting, by the second machine learning model, a keyword from the dataset based on regular expressions generated with predetermined rules.

According to an embodiment of the non-transitory computer-readable medium, wherein the second machine learning model is a second self-learning model comprising a second feedback layer that enables the second machine learning model to learn continuously from the dataset.

According to an embodiment of the non-transitory computer-readable medium, wherein the keyword comprises a clinical outcome assessment name.

According to an embodiment of the non-transitory computer-readable medium, the medium and the computer system are further configured for assigning a weight to the keyword based on a first pattern of outcomes of historical datasets.

According to an embodiment of the non-transitory computer-readable medium, the medium and the computer system are further configured for modifying the weight of the keyword based on a second pattern of outcomes of training datasets.

According to an embodiment of the non-transitory computer-readable medium, the medium and the computer system are further configured for performing word frequency analysis on the dataset to determine word frequency in the dataset; and optimizing the keyword in the dataset based on the word frequency.

According to an embodiment of the non-transitory computer-readable medium, the medium and the computer system are further configured for identifying the keyword having a word frequency above a threshold; and updating the keyword based on words not included in the keyword from the dataset extracted based on the regular expressions and having a higher than a threshold word frequency.

According to an embodiment of the non-transitory computer-readable medium, the medium and the computer system are further configured for validating the keyword; and generating an indication that the keywords are validated.

According to an embodiment of the non-transitory computer-readable medium, the medium and the computer system are further configured for performing data curation of the keyword.

According to an embodiment of the non-transitory computer-readable medium, the data curation comprises a rule-based algorithm to reconcile and harmonize the keyword based on a second predefined threshold value.

According to an embodiment of the non-transitory computer-readable medium, the rule-based algorithm comprises natural language processing (NLP) algorithm.

BRIEF DESCRIPTION OF THE FIGURES

These and other aspects of the present invention will now be described in more detail, with reference to the appended drawings showing exemplary embodiments of the present invention, in which:

FIG. 2 illustrates a flow chart describing a method of tracking a clinical outcome assessment according to an embodiment.

Figure 1:
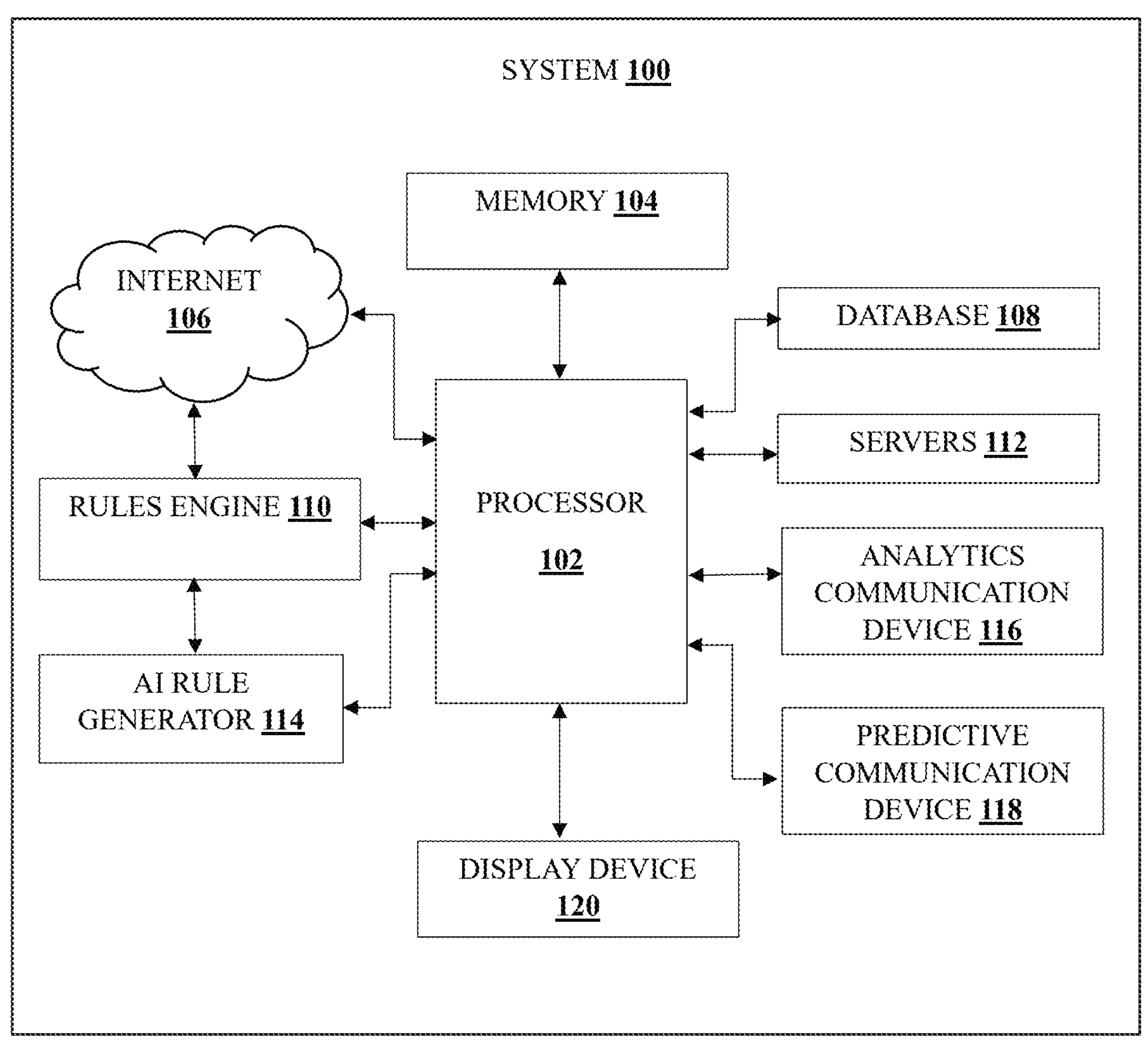
FIG. 1 is a diagram illustrating a system for tracking clinical outcome assessments in clinical studies and publications, according to one or more embodiments.

Other features of the present embodiments will be apparent from the accompanying drawings and from the detailed description that follows.

DETAILED DESCRIPTION

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numeral in different figures denotes the same elements.

Although the detailed description herein contains many specifics for the purpose of illustration, a person of ordinary skill in the art will appreciate that many variations and alterations to the details are considered to be included herein.

Accordingly, the embodiments herein are without any loss of generality to, and without imposing limitations upon, any claims set forth. The terminology used herein is for the purpose of describing particular embodiments only and is not limiting. Unless defined otherwise, all technical and scientific terms used herein have the same meaning as commonly understood by one with ordinary skill in the art to which this disclosure belongs. The following terms and phrases, unless otherwise indicated, shall be understood to have the following meanings.

As used herein, the articles "a" and "an" used herein refer to one or to more than one (i.e., to at least one) of the grammatical object of the article. By way of example, "an element" means one element or more than one element. Moreover, usage of articles "a" and "an" in the subject specification and annexed drawings construe to mean "one or more" unless specified otherwise or clear from context to mean a singular form.

As used herein, the terms "example" and/or "exemplary" mean serving as an example, instance, or illustration. For the avoidance of doubt, such examples do not limit the herein described subject matter. In addition, any aspect or design described herein as an "example" and/or "exemplary" is not necessarily preferred or advantageous over other aspects or designs, nor does it preclude equivalent exemplary structures and techniques known to those of ordinary skill in the art.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent, or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As used herein, two or more elements or modules are "integral" or "integrated" if they operate functionally together. Two or more elements are "non-integral" if each element can operate functionally independently.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

As used herein, the term "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value. As used herein the term "component" refers to a distinct and identifiable part, element, or unit within a larger system, structure, or entity. It is a building block that serves a specific function or purpose within a more complex whole. Components are often designed to be modular and interchangeable, allowing them to be combined or replaced in various configurations to create or modify systems. Components may be a combination of mechanical, electrical, hardware, firmware, software, and/or other engineering elements.

Digital electronic circuitry, or computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a stand-alone program or a module, component, subroutine, or other unit suitable for use in a computing environment may deploy it. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD-ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship with each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/or modules and/or other electronic devices. The term network may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Controller (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable sub-combination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multi-tasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

As used herein, the term "unauthorized access" is when someone gains access to a website, program, server, service, or other system using someone else's account or other methods. For example, if someone kept guessing a password or username for an account that was not theirs until they gained access, it is considered unauthorized access.

As used herein, the term "IoT" stands for Internet of Things which describes the network of physical objects "things" or objects embedded with sensors, software, and other technologies for the purpose of connecting and exchanging data with other devices and systems over the internet.

As used herein "machine learning" refers to algorithms that give a computer the ability to learn without explicit programming, including algorithms that learn from and make predictions about data. Machine learning techniques include, but are not limited to, support vector machine, artificial neural network (ANN) (also referred to herein as a "neural net"), deep learning neural network, logistic regression, discriminant analysis, random forest, linear regression, rule-based machine learning, Naïve Bayes, nearest neighbor, decision tree, decision tree learning, and hidden Markov, etc. For the purposes of clarity, part of a machine learning process can use algorithms such as linear regression or logistic regression. However, using linear regression or another algorithm as part of a machine learning process is distinct from performing a statistical analysis such as regression with a spreadsheet program. The machine learning process can continually learn and adjust the classifier as new data becomes available and does not rely on explicit or rule-based programming. The ANN may be featured with a feedback loop to adjust the system output dynamically as it learns from the new data as it becomes available. In machine learning, backpropagation and feedback loops are used to train the Artificial Intelligence/Machine Learning (AI/ML) model improving the model's accuracy and performance over time. Statistical modeling relies on finding relationships between variables (e.g., mathematical equations) to predict an outcome.

As used herein, the term "data mining" is a process used to turn raw data into useful information. It is the process of analyzing large datasets to uncover hidden patterns, relationships, and insights that can be useful for decision-making and prediction.

As used herein, the term "data acquisition" is the process of sampling signals that measure real world physical conditions and converting the resulting samples into digital numeric values that a computer manipulates. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "dashboard" is a type of interface that visualizes particular Key Performance Indicators (KPIs) for a specific goal or process. It is based on data visualization and infographics.

As used herein, a "database" is a collection of organized information so that it can be easily accessed, managed, and updated. Computer databases typically contain aggregations of data records or files.

As used herein, the term "data set" (or "dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

As used herein, a "sensor" is a device that detects and measures physical properties from the surrounding environment and converts this information into electrical or digital signals for further processing. Sensors play a crucial role in collecting data for various applications across industries. Sensors may be made of electronic, mechanical, chemical, or other engineering components. Examples include sensors to measure temperature, pressure, humidity, proximity, light, acceleration, orientation etc.

The term "communication module" or "communication unit" or "communication system" as used herein refers to a system which enables the information exchange between two points. The process of transmission and reception of information is called communication. The elements of communication include but are not limited to a transmitter of information, channel or medium of communication and a receiver of information.

The term "autonomous communication" as used herein comprises communication over a period with minimal supervision under different scenarios and is not solely or completely based on pre-coded scenarios or pre-coded rules or a predefined protocol. Autonomous communication, in general, happens in an independent and an unsupervised manner. In an embodiment, a communication module is enabled for autonomous communication.

The term "communication connection" or "communication network" as used herein refers to a communication link. It refers to a communication channel that connects two or more devices for the purpose of data transmission. It may refer to a physical transmission medium such as a wire, or to a logical connection over a multiplexed medium such as a radio channel in telecommunications and computer networks. A channel is used for the information transfer of, for example, a digital bit stream, from one or several senders to one or several receivers. A channel has a certain capacity for transmitting information, often measured by its bandwidth in Hertz (Hz) or its data rate in bits per second.

The term "communication" as used herein refers to the transmission of information and/or data from one point to another. Communication may be by means of electromagnetic waves. Communication is also a flow of information from one point, known as the source, to another, the receiver. Communication comprises one of the following: transmitting data, instructions, information or a combination of data, instructions, and information. Communication happens between any two communication systems or communicating units.

The term "protocol" as used herein refers to a procedure required to initiate and maintain communication; a formal set of conventions governing the format and relative timing of message exchange between two communications terminals; a set of conventions that govern the interactions of processes, devices, and other components within a system; a set of signaling rules used to convey information or commands between boards connected to the bus; a set of signaling rules used to convey information between agents; a set of semantic and syntactic rules that determine the behavior of entities that interact; a set of rules and formats (semantic and syntactic) that determines the communication behavior of simulation applications; a set of conventions or rules that govern the interactions of processes or applications between communications terminals; a formal set of conventions governing the format and relative timing of message exchange between communications terminals; a set of semantic and syntactic rules that determine the behavior of functional units in achieving meaningful communication; a set of semantic and syntactic rules for exchanging information.

The term "communication protocol" as used herein refers to standardized communication between any two systems. An example communication protocol is a machine-to-machine (M2M) protocol. These protocols are adapted for diverse applications and network environments, such as in health management, ensuring interoperability, reliability, and security. Among the notable M2M protocols are MQTT (Message Queuing Telemetry Transport), CoAP (Constrained Application Protocol), and AMQP (Advanced Message Queuing Protocol).

The term "bidirectional communication" as used herein refers to an exchange of data between two components. In an example, the first component can be a remote patient monitoring device, such as an Internet of Things (IoT) sensor, that can automatically collect health metrics like heart rate, blood pressure, etc. and the second component can be a software application where healthcare professionals and/or patients can view the information.

The term "in communication with" as used herein, refers to any coupling, connection, or interaction using signals to exchange information, message, instruction, command, and/or data, using any system, hardware, software, protocol, or format regardless of whether the exchange occurs wirelessly or over a wired connection.

The terms "non-transitory computer-readable medium" and "computer-readable medium" include a single medium or multiple media such as a centralized or distributed database, and/or associated caches and servers that store one or more sets of instructions. Further, the terms "non-transitory computer-readable medium" and "computer-readable medium" include any tangible medium that is capable of storing, encoding, or carrying a set of instructions for execution by a processor that, for example, when executed, cause a system to perform any one or more of the methods or operations disclosed herein. As used herein, the term "computer-readable medium" is expressly defined to include any type of computer-readable storage device and/or storage disk and to exclude propagating signals.

The term "application server" refers to a server that hosts applications or software that delivers a business application through a communication protocol. An application server framework is a service layer model. It includes software components available to a software developer through an application programming interface. It is system software that resides between the operating system (OS) on one side, the external resources such as a database management system (DBMS), communications and Internet services on another side, and the users' applications on the third side.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers-say, 'A' is '01', 'B' is '02', and so on. For example, a message like "HELLO" will be encrypted as "0805121215," and this value will be transmitted over the network to the recipient (s).

The term "decrypt" used herein refers to the process of converting an encrypted message back to its original format. It is generally a reverse process of encryption. It decodes the encrypted information so that only an authorized user can decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damaging data, stealing data, or disrupting digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attacks, data breaches, Denial of Service (DoS) attacks, and other attack vectors.

The term "hash value" used herein can be thought of as fingerprints for files. The contents of a file are processed through a cryptographic algorithm, and a unique numerical value, the hash value, is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application.

The term "alarm" as used herein refers to a trigger when a component in a system or the system fails or does not perform as expected. The system may enter an alarm state when a certain event occurs. An alarm indication signal is a visual signal to indicate the alarm state. For example, when a cyber security threat is detected, a system administrator may be alerted via sound alarm, a message, a glowing LED, a pop-up window, etc. Alarm indication signal may be reported downstream from a detecting device, to prevent adverse situations or cascading effects.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

The embodiments described herein can be directed to one or more of a system, a method, an apparatus, and/or a computer program product at any possible technical detail level of integration. The computer program product can include a computer-readable storage medium (or media) having computer-readable program instructions thereon for causing a processor to carry out aspects of the one or more embodiments described herein.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

As used in this application, the terms "component," "system," "platform," "interface," and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer-readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud-computing system.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when used as a transitional word in a claim.

As referred herein, "clinical trial" is a research study in which one or more trial subjects are prospectively assigned to one or more interventions (which may include placebo or other control) to evaluate the effects of those interventions on health-related biomedical or behavioural outcomes.

As referred herein, "Case Report Form" or "CRF" is a printed, optical, or electronic document designed to record all the protocol-required information to be reported to the sponsor for each patient participating in the study.

As referred herein, "monitoring" or "clinical trial monitoring" refers to an act of overseeing the process of a clinical trial, and of ensuring that it is conducted, recorded, and reported in accordance with the protocol, Standard Operating Procedures (SOP), Good Clinical Practice (GCP) and the applicable requirements. (ICH E6 Glossary).

The term "dataset" may be used broadly to refer to any data or collection of data, inclusive of but not limited to structured data (including tabular data or data encoded in JavaScript Object Notation (JSON) or other formats and so on), unstructured data (including documents, reports, summaries and so on), partial or subset data, incremental data, pooled data, simulated data, synthetic data, or any combination or derivation thereof. Certain examples are depicted or described herein in an exemplary sense without limiting the present disclosure to other forms of data or collection of data.

As used herein, "Artificial intelligence" or "AI" refers to the ability of a digital computer or computer-controlled robot to perform tasks commonly associated with intelligent beings.

As used herein, "pre-clinical research" refers to early use of AI in pre-clinical research, impacting subsequent clinical trials.

As used herein, "design" refers to use of AI enabling prediction of outcomes and disease progression to shape or improve Design of clinical trials.

As used herein, "recruitment" refers to the use of AI in Recruitment, which includes Enrollment, defined as the identification of eligible sites and eligible participants and onboarding them into suitable clinical trials.

As used herein, "conduct" refers to the period following a participant's enrollment into the trial, up-to the trial database lock, prior to statistical analysis.

The term "artificial intelligence unit" refers to any system that perceives its environment and takes actions that maximize its chance of achieving its goals. Artificial intelligence unit utilizes a plurality of machine learning algorithms that allow systems to automatically improve through experience and self-learning.

The term "feature" as used herein, in relation to machine learning and pattern recognition, represents or refers to an individual measurable property or characteristic of a phenomenon. Features are usually numeric, but structural features such as strings and graphs are used in syntactic pattern recognition. The concept of "feature" is related to that of explanatory variables used in statistical techniques such as linear regression.

As used herein "anonymization" refers to the process of turning data into a form that does not identify and recognize individuals. Anonymization breaks the link between data and a given participant so that the participant cannot be identified, directly or indirectly (e.g., through cross-referencing), from their data.

As used herein "clinical endpoint" refers to an event or outcome in clinical trials that can be measured objectively to determine whether the intervention being studied is beneficial. The endpoints of a clinical trial are usually included in the study objectives. An endpoint is a targeted outcome of a clinical trial that is statistically analyzed to help determine the efficacy and safety of the therapy being studied. Endpoints for a clinical trial may include one or more clinical outcome assessments. Some examples of endpoints are survival, improvements in quality of life, relief of symptoms, and disappearance of the tumor.

As used herein "clinical outcome assessment" or "COA" refers to a measure that describes or reflects how a patient feels, functions, or survives. Clinical outcome assessment (COA) measures the change in a clinical outcome and can be reported by a health care provider, a patient, a non-clinical observer (such as a parent), or through performance of an activity or task. For example, a clinical endpoint of a clinical trial studying a new therapy may be reducing the number of hospitalizations for respiratory distress. In this case, the clinical outcome is hospitalizations for respiratory distress. The COA will be the tool used to quantify the number of hospitalizations for respiratory distress for each participant of the study. Types of COAs may include Patient-reported outcome (PRO) measures, Clinician-reported outcome (ClinRO) measures, Observer-reported outcome (ObsRO) measures, and Performance outcome (PerfO) measures.

As used herein "sponsor" or "clinical trial sponsor" refers to an individual, company, institution, group, or organization that takes responsibility for the initiation, management, and/or financing of a clinical study or trial, and further collects and analyzes the data.

As used herein, the term "clinical data" refers to information related to the health status of patients and the care they receive within healthcare settings. This data encompasses a wide range of information collected during routine clinical care and is used for diagnosing, treating, and monitoring patients. Clinical data may include patient demographics, detailed medical history records, family medical history, and known allergies. Clinical data may further include clinical observations, diagnostic test results, and treatment information, health monitoring data, behavioral and lifestyle information, and patient-reported outcomes. Clinical data may further include administrative data, including appointment schedules, billing information, insurance details, and patient referrals, and support the efficient delivery of healthcare services.

As used herein, the term "medical data" may refer to data that include all that is included in clinical data, health data/information, and further, administrative data comprising insurance information, billing and insurance claims data, appointment and scheduling information, patient surveys, patient-reported outcomes, and patient satisfaction.

As used herein, the term "curated dataset" is a collection of data that has been meticulously organized, cleaned, and verified for quality and relevance. This process involves data collection, data cleaning, data transformation, data integration, data validation, data annotation and data reduction to ensure that the dataset is accurate, consistent, and useful for analysis or modeling. The result of the curation process is a high-quality dataset that is ready for analysis, modeling, or other applications. Curated datasets are valuable because they reduce the noise and errors present in raw data, derived data, manipulated data, and trained data, making it easier to derive meaningful insights and build reliable models.

As used here, the term "feature vector/s" are representations of data used to capture the essential characteristics or attributes of input data in a format that algorithms can process. Each element in a feature vector represents a specific feature (or attribute) of the data, quantified in a way that is meaningful for analysis.

As used herein, "feature engineering" with reference to artificial intelligence refers to the process of using domain knowledge to create input variables, or features, that make machine learning algorithms work more effectively. This process involves selecting, modifying, or creating new features from raw data to improve the performance and accuracy of predictive models. Effective feature engineering may significantly enhance the ability of machine learning models to identify patterns and make accurate predictions by providing the models with the most relevant and informative variables.

Business problem: Clinical Outcome Assessments (COAs) are instruments/processes/techniques centered on assessing how patients feel, function, and survive. For a successful development of a new intervention (drug or device), sponsors have to carefully choose and design how to use COAs in their clinical studies, i.e., their COA strategy. Obtaining COA information with current solutions is a very time-consuming process. This incurs significant costs by provoking delays in clinical study start-up. Because current solutions are not exhaustive, sponsors can miss important COA information, which can lead to poor COA strategy design and potential failure to meet clinical endpoints and/or regulatory approval. Clinical Research Organizations (CROs) provide literature review and COA strategy consultancy services to sponsors; however, data curation is still performed manually and specifically for each project. Therefore, there is a need for an innovative solution for obtaining COA information.

Technical problem: COA tracking is a very costly and complex task which involves reviewing and curating data from scientific publications, clinical trial repositories and regulatory agency websites to identify which COAs have been developed, which COAs should be developed, which COAs have been used in clinical studies and have evidence supporting their intended use and which COAs are suitable for what populations (language, culture, literacy). As the body of literature is ever-growing, COA tracking is a very time-consuming and exhaustive task, and it becomes manually impossible to keep up-to-date. Currently, the data curation is performed manually and specifically for each project. Manual data curation can incur significant costs for sponsors by provoking delays in clinical studies and unmet clinical endpoints due to suboptimal COA strategy design. Even with solutions using software, designed to speed up the literature review, the extracted data is reviewed manually and the process is specific to each project.

Business solution: An optimized data curation pipeline augmented by Artificial Intelligence (AI) models that track COAs in scientific publications and clinical trial repositories. The present disclosure provides a mechanism to a formally described model, which tackles the above-mentioned challenges and provides an overview of a possible COA strategy design to the sponsors before engaging in a full COA strategy analysis and development. The business solution involves creating a suite of AI-driven tools that can be used to track clinical outcome assessments.

Technical solution: A data curation pipeline consisting of machine learning models to automate the extraction of COA information from clinical studies, descriptions, and scientific publications and to provide a system that curates COA information at one place to help build COA strategy design. To address the above limitations, the technological solution (i.e., integrating advanced technologies, such as artificial intelligence (AI) and machine learning models to enhance the accuracy and efficiency) provides optimized data curation pipelines augmented by AI models to track COAs.

When developing a new intervention (drug or device), Pharmaceutical, Biotech and Medical device companies perform clinical studies to provide evidence on the treatment benefit and risks to get regulatory approval on the market. Used in clinical endpoints, Clinical Outcome Assessments (COAs) are instruments centered on assessing how patients feel, function, and survive. Consideration of the patient's perspective is increasingly required by regulatory authorities and therefore COAs are now a key part of any new therapy evaluation. For a successful development, sponsors have to carefully choose and design how to use COAs in their clinical studies, i.e., their COA strategy.

Currently, there is no technology that systematically tracks COAs in clinical publications or clinical trial repositories. The software solutions available are not specific to the COA field and do not have sufficient accuracy, recall or precision for the intended use. Therefore, data provided by existing solutions still needs substantial time-consuming manual review. Due to this lack of technology, there is also no solution existing that curates all needed COA information at one place. Sponsors need to use multiple solutions to build their COA strategy, including subscribing to databases, paying for literature review software, and/or commissioning external consultancy services, and manually reconciling data. Therefore, there is a long-felt need from the industry for the following reasons:

Obtaining COA information with existing solutions is a very time-consuming process. This incurs significant costs by provoking delays in clinical study start-up.

Because current solutions are not exhaustive, sponsors can miss important COA information, which can lead to poor COA strategy design and potential failure to meet clinical endpoints and/or regulatory approval. Sponsors might also engage significant costs to develop new COAs from scratch for their study when it might have been possible to adapt and modify existing ones.

Further, there is no existing COA standard naming convention or ontology, which makes it difficult to automate the systematic tracking of COAs in different sources of information, as it is very challenging to reconcile different COA naming for the same COA in different sources.

Technical Result: The disclosure provides machine learning algorithms developed to automate the data extraction of COA names in clinical studies, descriptions from clinical repositories such as ClinicalTrials.gov (CT.gov), and abstracts of scientific publications such as PubMed. One data curation pipeline has been conceptualized for COAs in clinical repositories, and another data curation pipeline for COAs in scientific publications. A COA may be present in multiple different forms in clinical outcomes and scientific publications, such as in the form of a questionnaire, an assessment, an instrument, a tool, a form, a score, a scale, an index, or a rating. The system of tracking clinical outcome assessment in clinical studies and scientific publications is provided utilizing machine learning models. Accordingly, a classifier model has been developed to determine whether the clinical trial outcome contains a description of a clinical outcome assessment or not. This may reduce the number of clinical trials to be screened to extract COA names. The clinical trials identified as describing COAs by the classifier model are fed to a Large Language Model (LLM) that extracts COA names from the outcome text (outcome title and/or description). As COA names can be described in many ways and spellings by different researchers, to analyze COA-related information, data needs to be reconciled for the same COA across trials and outcomes. A rule-based algorithm using Natural Language Processing (NLP) reconciles and harmonizes the COA names. The system thus provides an optimized data curation pipeline augmented by AI models that track COAs in scientific publications and a data curation pipeline augmented by AI models that track COAs in clinical trial repositories How a Technical Solution is a Technological Advancement: The system is designed to address the challenge faced to track COAs from clinical studies repositories and publications. The system leverages advanced technologies, including machine learning, artificial intelligence, and different machine learning techniques together providing an end-to-end solution to track COAs. The system provides automatic extraction and harmonization of COA names from text obtained from different sources and the ability to analyze associated data in one solution.

Technical Details Specific to the Technical Solution: FIG. 1 illustrates a block diagram of a system for tracking clinical outcome assessments in clinical studies and publications.

Referring to FIG. 1 the system 100 comprises processor 102, memory 104, linked to the Internet 106, a rules engine 110 and an AI rule generator 114. The processor 102 further links a database 108, servers 112, an analytics communication device 116, a predictive communication device 118, and a display device 120.

Referring to FIG. 1, processor 102 may be a high-performance, multi-core CPU or system-on-chip (SoC) solution to process vast amounts of data. In some embodiments, processor 102 processes data from memory 104, database 108, and other inputs to make real-time decisions related to tracking of clinical outcomes. Processor 102 may comprise Graphics Processing Units (GPUs). GPUs are utilized for their ability to accelerate tasks like data processing. The processor may depend on aspects such as processing requirements and power consumption. Processors, also known as central processing units (CPUs), are the heart and brain of any computer or electronic device capable of executing instructions. Processor or processors' function is to process data and perform calculations, etc. At the core of their operation lies data processing, where they handle arithmetic and logical operations on data stored in memory. CPUs execute instructions, which are sets of specific operations encoded in machine language, to perform various tasks. The control unit within, or interacting with, the processor manages and coordinates the execution of instructions, fetching them from memory, decoding them, and directing the appropriate components to execute the instructions. To ensure a controlled and orderly flow of tasks, processors use an internal clock that generates regular electrical pulses, synchronizing their operations through clock cycles. Processors support multitasking environments, rapidly switching between executing different tasks for various applications. Additionally, they may work with the operating system to manage virtual memory, allowing programs to access more memory than is physically available, and to efficiently manage memory usage. Processor or processors may be integrated with security features, including hardware-level encryption, memory protection, and support for secure execution environments, enhancing the system's security against potential threats. The processor may run sophisticated algorithms and artificial intelligence (AI) software to analyze input data, interpret the environment, and help in decision-making. In an embodiment, the processor may be a neuromorphic processor, inspired by the human brain, which offers a unique approach to handling AI tasks. Processor 102 interacts, exchanges data, controls, and coordinates with one or more of the other components or modules of the system, and computes and processes the tracking of clinical outcomes.

Referring to FIG. 1, memory 104 may be a non-volatile memory (NVM) which is utilized in reliable operations of the system, ensuring that data is preserved even during power interruptions or failures. Various NVM technologies are utilized, such as flash memory for storing the operating system and software, EEPROM for retaining configuration data, calibration values, and sensor settings, Ferroelectric RAM (FRAM) for critical real-time information, and emerging technologies like ReRAM for potential performance enhancements due to its high-speed operation and low power consumption. In an embodiment, the memory may be a cloud-based memory. In another embodiment, the memory may be a local memory. In another embodiment, the memory may be a combination of local and cloud-based memory. Local memory refers to the traditional memory components present in a physical device, such as a computer's RAM, hard disk drives (HDDs), or solid-state drives (SSDs). It provides fast access to data, making it suitable for immediate processing tasks and offline use. On the other hand, cloud-based memory relies on remote servers and services provided by third-party cloud providers to store and manage data over the internet. Systems can access their data from anywhere with an internet connection, allowing for seamless collaboration and scalability. Cloud-based memory is often used for storing large amounts of data, enabling data sharing, and providing backup and disaster recovery solutions. The combination of local memory and cloud-based memory allows for flexible and efficient data management tailored to different needs of the system.

The rules engine 110 may be configured to execute one or more rules, e.g., in a planned, scheduled, and/or ordered manner. The rules may be generated by the AI rule generator 114, which uses artificial intelligence to formulate rules to enable future oriented tracking of clinical outcome assessments. The rules enable the various pipelines to be triggered. The servers 112 may be configured in hardware terms according to the specified requirements in the clinical outcome assessments tracking network. In one example, the servers have a speed in the range of 2 to 3 GHZ, have 4 to 16 cores, and a memory capacity of 12 to 15 GB. However, the parameters may be different, depending on the capacity requirements. The analytics communication device 116 and predictive communication device 118 may include diverse technologies for collection, processing, storage, and distribution of data such as Smart Phones, iPads, Desktop/Personal Computers, Stand-alone/On-Premise/Cloud Servers, and the like. Each device and server comprise digital data processors and communication interfaces as is well-known in the art. Planning and forecasting, carried out by the analytics communication device 116 and predictive communication device 118, gives estimates of occurrences of COAs, which may help predict the probability of COA occurrences.

The servers 112 may include servers that model, manage, analyze, and predict the tracking of clinical outcome assessments. The devices 116 and 118 may continually interface with the database 108 and apply algorithms to provide trends and predictions as to the likely clinical outcome assessment tracking strategy. The outcome of the trends and the predictions may be displayed on the display device 120. In some embodiments, database 108 may be locally present in system 100 or may be present in a cloud server. The data stored in the database may be fetched and displayed on the display device 120. The system ecosystem may have various components with a suite of Artificial Intelligence algorithms developed using software such as Python and R. The database 108 may comprise a data anonymization unit which anonymizes or pseudonymizes the inputs received by discarding the metadata, such as patient details, associated with the inputs. Anonymization may be performed to break the link between data and a given participant so that the participant cannot be identified, directly or indirectly. Such an anonymization can be performed based on rules which are preconfigured or configured at the time of data transfer. The patient's details may contribute to determining the identity or recognizing the patient. Key patient identifiable fields, such as, but not limited to, patient name and patient ID, address, social security number, credit card information, etc., need to be anonymized before the patient medical data can be used. Once the data is anonymized, the patient identity is concealed such that one cannot trace or track the source (e.g., patient identity, site identity, etc.) of the medical data. In an embodiment, the data anonymization unit anonymizes the inputs by removing facial detection information and biometrics information from the inputs. The database technology may be instantiated as a Relational Database Management System (RDBMS) or as an in-memory data grid spanning clusters of servers to allow for faster throughput and real-time processing of events as they occur during the tracking of clinical outcome assessments. The deployment of the database(s) may be in a private data center on a secured public cloud infrastructure to allow for quick scale up during periods of intense activity where the volumes of data approach that of a data stream and may require additional infrastructure to support spikes in demand during these periods. Designing and developing such a complex computation system for predicting clinical outcome assessments utilizes a software ecosystem/platform with robust computational infrastructure.

As an example, the model may be based on a network of interconnected nodes representing domain specific COA information. The edges represent the influence one node has on another node. This may be represented in Resource Description Framework (RDF) and stored in a graph or relational database. The node used in the subject of an RDF statement may be a blank node. The resources indicated by blank nodes are anonymous resources. The blank node or bnode may represent a subject about which, other than the relationship, nothing else is known. The ontology that may be built would be customizable for a study by a clinical trial sponsor, stored and referenced in such a way that the model may be reused and enriched by subsequent application in more and more COA tracking studies. The data that would act as the training dataset for the initial implementation may use the results of previous studies. An exercise may be undertaken to gather the metadata associated with the tracking of a COA in a clinical trial repository or a scientific publication. Once the metadata is gathered, an artificial intelligence (AI)/machine learning (ML) model may be trained with the metadata using the rules engine 110, the AI rule generator 114, the analytics communication device 116, and predictive communication device 118 of the system 100. The AI/ML model synthesizes large data volumes. In addition, the AI/ML predicts output in a substantially reduced time period, wherein the time period can be just seconds. The AI/ML model predicts the output in a substantially reduced timeframe than what could be performed by humans in a cloud-computing platform.

FIG. 2 illustrates a flow chart describing a method for tracking clinical outcome assessments.

In some embodiments, the method shown in FIG. 2 may be carried out by a processor using instructions stored in a memory that, when executed, causes the processor to carry out the method. In an embodiment, the method as shown in FIG. 2 may be performed by system 100 as shown in FIG. 1.

Figure 3:
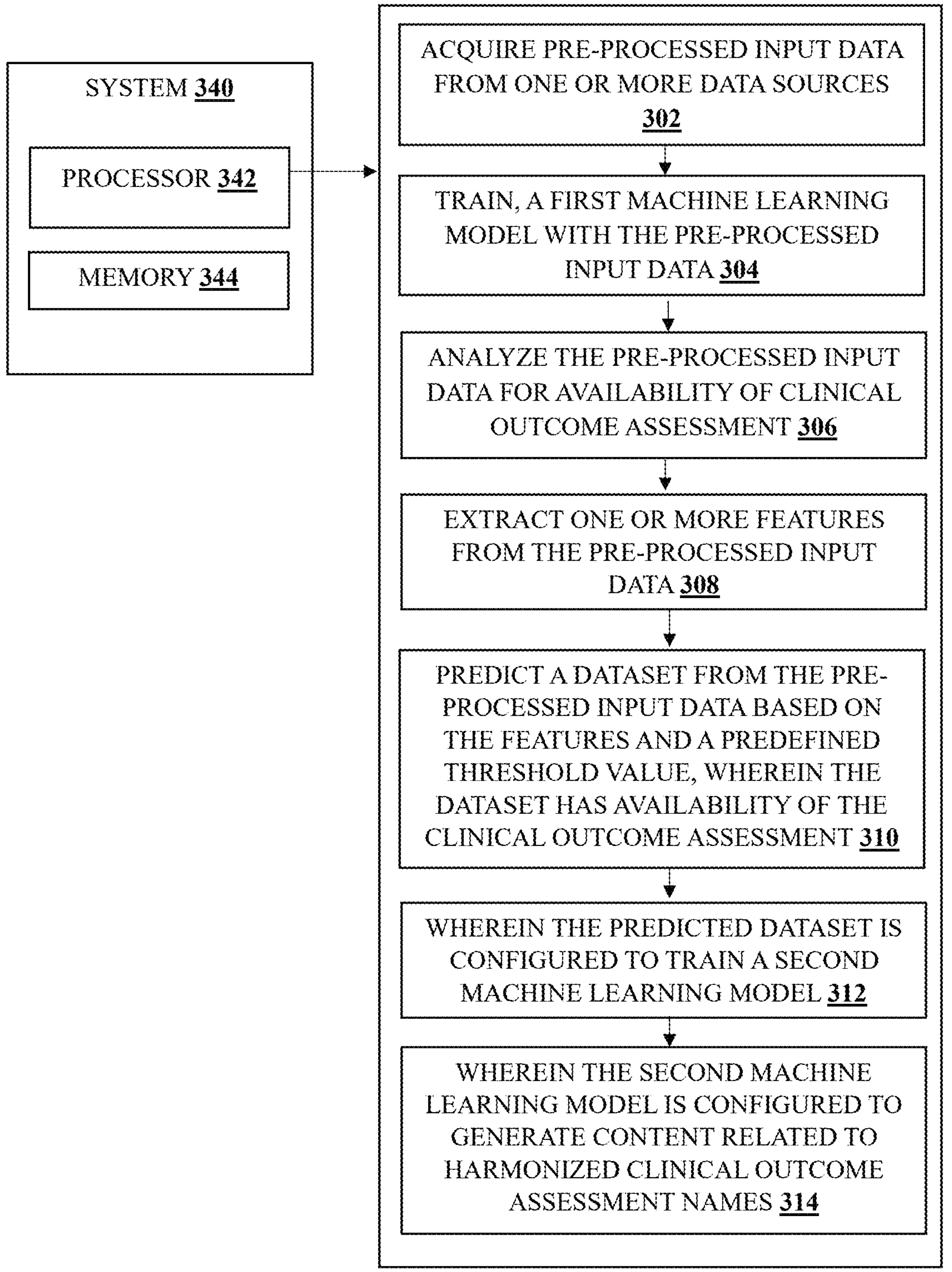
FIG. 3 illustrates steps executed by a system according to an embodiment.

Referring to FIG. 2, the method may, at step 202 acquire pre-processed input data from one or more data sources. Method may, at step 204, train a first machine learning model with the pre-processed input data. The method may, at step 206, analyze the pre-processed input data for availability of clinical outcome assessment. The method may, at step 208, extract one or more features from the pre-processed input data. The method may, at step 210, predict a dataset from the pre-processed input data based on the features and a predefined threshold value, wherein the dataset has availability of the clinical outcome assessment. The method may, at step 212, wherein the predicted dataset is configured to train a second machine learning model. The method may, at step 214, wherein the second machine learning model is configured to generate content related to harmonized clinical outcome assessment names. FIG. 3 illustrates a block diagram of the system implementing the method according to an embodiment. According to an embodiment, disclosed is system 340 comprising processor 342, and memory 344, wherein the memory 344 storing processor-executable instructions, which on execution, cause the processor to: acquire pre-processed input data from one or more data sources 302, train, a first machine learning model with the pre-processed input data 304, analyze the pre-processed input data for availability of clinical outcome assessment 306, extract one or more features from the pre-processed input data 308, predict a dataset from the pre-processed input data based on the features and a predefined threshold value, wherein the dataset has availability of the clinical outcome assessment 310, wherein the predicted dataset is configured to train a second machine learning model 312, and wherein the second machine learning model is configured to generate content related to harmonized clinical outcome assessment names 314.

According to an embodiment of the system, the pre-processed input data comprises at least one of structured data, semi-structured data, and unstructured data. According to an embodiment of the system, the data sources comprise at least one of a clinical study description, a scientific publication, a research publication, a clinical investigation, and a clinical research study. According to an embodiment of the system, the pre-processed input data from the data sources is stored in a database.

According to an embodiment of the system, the data sources comprise at least one of a textual data, a numerical data, a graphical representation, a chart, and a table.

According to an embodiment of the system, the first machine learning model is further configured to: cleanse and filter the pre-processed input data based on at least one of an input from a user, and a predefined rule.

According to an embodiment of the system, the first machine learning model is configured to perform one or more of a normalization, a standardization, and a stratification of the pre-processed input data.

According to an embodiment of the system, the system is further configured to: customize the first machine learning model by at least one of manipulating the pre-processed input data, adding, modifying, and removing at least one node of the first machine learning model, and training the first machine learning model using the manipulated pre-processed input data.

According to an embodiment of the system, the system is further configured to: enable a user to interact with a server through a user interface, provided via a device associated with the user, and at least one of build, train, re-train, replicate, compare, and share the first machine learning model.

According to an embodiment of the system, the pre-defined threshold value is initially set based on at least one of outcomes of historical input data and predicted by the first machine learning model.

According to an embodiment of the system, the first machine learning model comprises at least one of a Random Forest classifier model, an XGBoost model, a Support Vector Machine (SVM) model, a Stochastic Gradient Descent model, and a Logistic Regression model.

According to an embodiment of the system, the first machine learning model further comprises a hard voting algorithm.

According to an embodiment of the system, the system is configured to display the dataset.

According to an embodiment of the system, the system is configured for tracking of the clinical outcome assessment.

According to an embodiment of the system, the first machine learning model is calibrated and selected from one or more artificial intelligence (AI) models for tracking of the clinical outcome assessment by evaluating AI model candidates against a set of performance criteria.

According to an embodiment of the system, the set of performance criteria comprise prediction accuracy, computational efficiency, and adaptability to diverse pre-processed input data.

According to an embodiment of the system, the processor is configured as a deep learning model for feature extraction.

According to an embodiment of the system, the processor is configured to stratify a feature into one of low, medium, and high relevance categories.

According to an embodiment of the system, the first machine learning model comprises a neural network comprising a non-linear activation function configured to capture a non-linear association with the input data.

According to an embodiment of the system, the first machine learning model is configured to learn using labelled data using a supervised learning model, wherein the supervised learning model comprises logic using at least one of a decision tree, a logistic regression, a support vector machine, a k-nearest neighbors, a Naïve Bayes, a random forest, a linear regression, a polynomial regression, and a support vector machine for regression.

According to an embodiment of the system, the first machine learning model is a self-learning model. A self-learning model is a model that after deploying may be optimized by training the model on data that becomes available over time. The self-learning model may be trained on the input data. As new data becomes available, it improves the self-learning model on a continuous basis by recording the data characteristics, test conditions, and test results. Further, the self-learning model improves based on the collected data which makes the model predictions more accurate, and the model uses self-learning to finetune its capabilities.

According to an embodiment of the system, the first machine learning model has a feedback loop, wherein an output from a previous step is fed back to the model in real-time to improve performance and accuracy of the output of a next step.

According to an embodiment of the system, the first machine learning model comprises a feedback loop, wherein the learning is further reinforced with a reward for each true positive of an output of the system.

According to an embodiment of the system, the processor is further configured to: train a second machine learning model with the dataset, wherein the second machine learning model is configured to, extract a keyword from the dataset based on regular expressions generated with predetermined rules According to an embodiment of the system, the second machine learning model is a second self-learning model comprising a second feedback layer that enables the second machine learning model to learn continuously from the updated dataset.

According to an embodiment of the system, the keyword comprises a clinical outcome assessment name.

According to an embodiment of the system, the processor is further configured to assign a weight to the keyword based on a first pattern of outcomes of historical datasets.

According to an embodiment of the system, the processor is further configured to modify the weight of the keyword based on a second pattern of outcomes of training datasets.

According to an embodiment of the system, the second machine learning model is further configured to: perform word frequency analysis on the dataset to determine word frequency in the dataset; and optimize the keyword in the dataset based on the word frequency.

According to an embodiment of the system, the second machine learning model is further configured to: identify the keyword having a word frequency above a threshold; and update the keyword based on words not included in the keyword from the dataset extracted, based on the regular expressions, and having a higher than the threshold word frequency.

According to an embodiment of the system, the second machine learning model is further configured to validate the keyword and generate an indication that the keyword is validated.

According to an embodiment of the system, the processor is further configured to perform data curation of the keyword.

According to an embodiment of the system, the data curation comprises a rule-based algorithm to reconcile and harmonize the keyword based on a second predefined threshold value.

According to an embodiment of the system, the rule-based algorithm comprises a natural language processing (NLP) algorithm.

Figure 4:
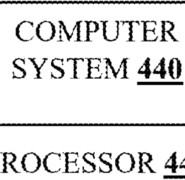
FIG. 4 illustrates a block diagram of the method executed by the non-transitory computer-readable medium according to an embodiment.

FIG. 4 illustrates a block diagram of the method executed by the non-transitory computer-readable medium according to an embodiment.

According to an embodiment, disclosed is non-transitory computer-readable medium 444 having stored thereon instructions executable by computer system 440 to perform operations comprising: acquiring pre-processed input data from one or more data sources at step 402, training, a first machine learning model with the pre-processed input data at step 404, analyzing the pre-processed input data for availability of clinical outcome assessment at step 406, extracting one or more features from the pre-processed input data at step 408, predicting a dataset from the pre-processed input data based on the features and a predefined threshold value, wherein the dataset has availability of the clinical outcome assessment at step 410, wherein the predicted dataset is configured to train a second machine learning model at step 412, and wherein the second machine learning model is configured to generate content related to harmonized clinical outcome assessment names at step 414. A software application 448 may be stored on non-transitory computer-readable medium 444 and executed by processor 442 of computer system 440.

Figure 5:
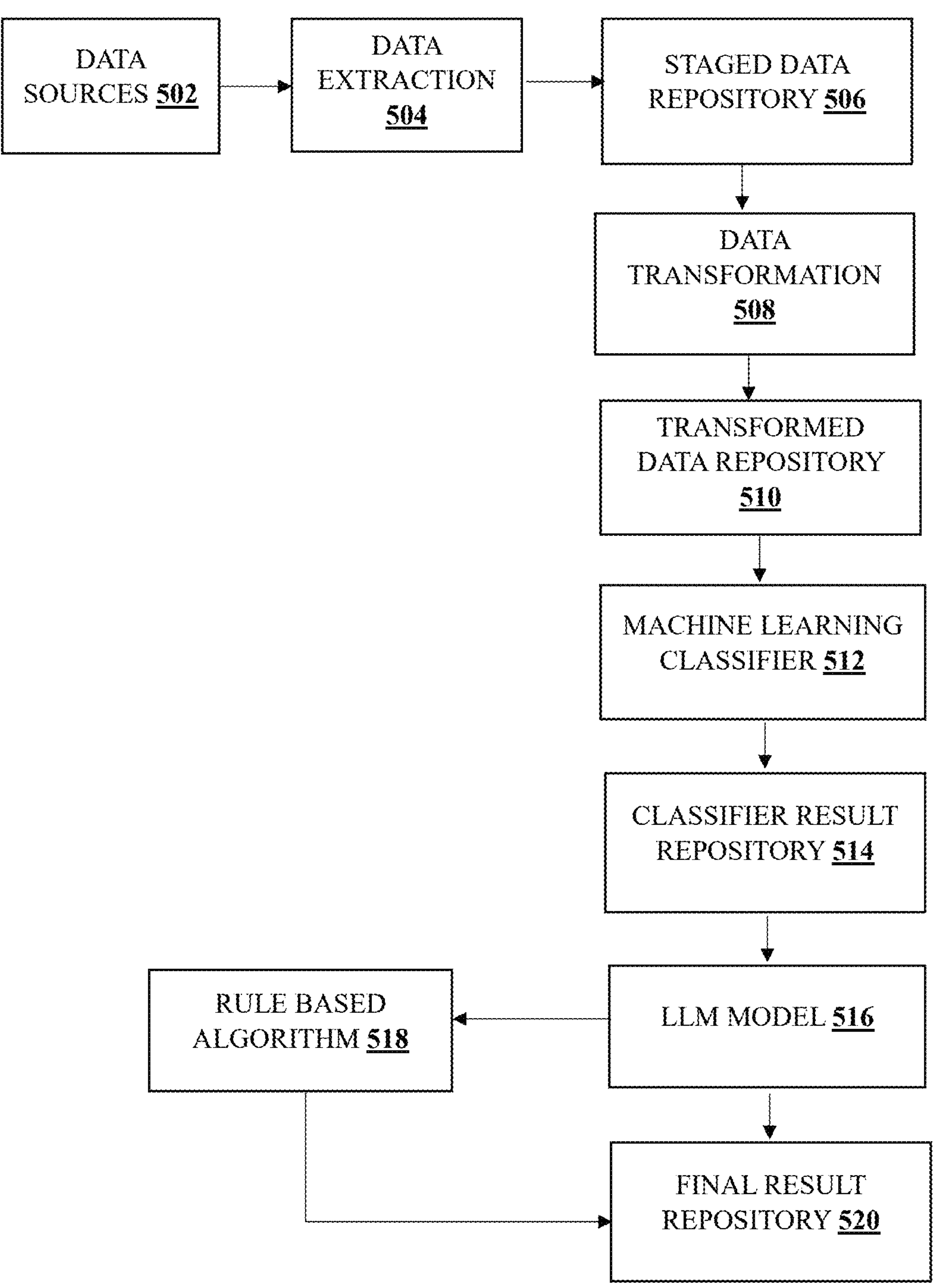
FIG. 5 illustrates overall data flow from source to final repository according to an embodiment.

FIG. 5 illustrates overall data flow from source to final repository according to an embodiment.

At step 502, data may be sourced from various data sources, such as clinical trial repositories and scientific publications. The data, at step 504, is extracted from the data sources using Application programming interfaces (APIs) of the data sources, the databases, or data export features of the data sources. At step 506, the extracted data may be moved to a staged data repository so as to carry out the required pre-processing on the data. At step 508, data transformation is applied to the data so as to make the data input ready for the machine learning classifier. The transformed data is moved to a transformed data repository at step 510. At step 512, the transformed data is input to the machine learning classifier. The output of the machine learning classifier is stored in a classifier result repository at step 514. The output of the classifier, the data containing the clinical outcomes, is input to the Large Language model (LLM) at step 516. At step 516, the system may extract COA names from the clinical outcomes using an LLM. The resulting output may consist of the extracted COA names. At step 518, the system may apply rule-based algorithms to the COA names in order to reconcile and harmonize COA names. The COA name generated may be input into the rule-based algorithm to determine if it matches any existing COAs in the database. The system may utilize a rule-based algorithm using Natural Language Processing (NLP) developed to reconcile the COA names with standard naming convention or ontology. At step 520, the final output is stored in a final result repository.

Usually, the input data is obtained from multiple sources and the data formats vary between sources depending upon how the data is stored and organized. The input data may be inaccurate, noisy, and inconsistent due to the nature of data acquisition processes and diversity of the nature of data. Therefore, the system runs its pre-processing algorithms that deal with processing both structured and unstructured data. These algorithms pre-process the structured and unstructured data and then forward the cleaned data to the subsequent modules for further processing and analysis. Some of the pre-processing approaches are:

Structured Data

Data Inaccuracy-handling the incomplete, missing values can be done using traditional techniques such as imputation with mean, normal values and also with model-based approaches such as multivariate regression and k-nearest neighbor. Data Noise-reducing noise by removing erroneous data and outliers from the data by multivariate approaches.

Data Inconsistency-identified when data is input from various sources. During this time, the source with the most inconsistent data can be identified and can be addressed using correlation analysis.

Unstructured Data

Notes/Text: For textual data, the normalization can be a task for analysis of clinical staffs' notes and laboratory reports. With normalization, the system handles some of the challenges in text processing such as:

Format/Code Conversion-data from multiple sources in various formats/codes can be collected and converted to simple format. The system incorporates Scripts for converting files in different formats to one standard format.

Eliminating Stop Words/Punctuations/Non-ASCII characters—The system incorporates regular expression scripts to eliminate the stop words, punctuations and non-ascii characters. Identifying Stem Words-reducing each word in the text to base or root will improve the analysis of textual data. The system comprises modules for performing stemming on clinical and laboratory notes.

Lemmatization—as used herein can refer to reducing words to base form by considering the context, along with the content, and can be useful in identifying clinical, biological entities in notes or reports. Alternatively, lemmatization of words helps to tag the text.

EDA-Exploratory Data Analysis: The system also considers the synthesized results pertaining to the factors associated with tracking COAs in clinical outcomes and scientific publications. These results can show the incidence and prevalence of the factors for COA occurrence besides providing deep insights into understanding the behavior of factors for different cohorts. Such an exploratory analysis can be used in designing the tracking of COAs. Results can be rendered by rich graphical presentations through a dashboard that enables easy interpretation and assessment of COA occurrence indicators. Some of the visualizations rendered in the dashboard are usually depicted using the charts speedometer, gauge meter and horizontal bar charts.

Training Data: In order to accurately select appropriate studies from a database, such as PubMed, a classifier model is built by training the model using a balanced dataset of publications (8000 publications). This set consists of an equal mix of relevant articles (4000 publications related to development and validation) and non-relevant articles (4000 publications unrelated to development or validation). Shrinking the training dataset may lead to poorer generalization in the model due to insufficient representation of the classes. In the PubMed database, with 36 million citations, merely 1-3% pertain to development/validation studies. Despite the dominance of negative class data, a minimum threshold of 4000 data points for this class may be sufficient to obtain satisfactory outcomes. The data for the positive class is sourced from a carefully assembled Database, which may contain a comprehensive list of current COAs. This COA database is primarily constructed using COAs derived from development or validation studies found in the PubMed database. For the negative class, each data point is individually chosen through a manual assessment of publications from PubMed, ensuring none are development or validation studies. The sample undergoes an additional round of review for confirmation that all 4000 data points are distinct. The model may be a self-learning model that has been trained on the input data and can improve robustness of the system and uncertainty estimation abilities.

In an embodiment, a sample training data may look like table 1 below:

TABLE 1

| S. No | Title | Abstract | COA | Text | Pre-processed text |
|---|---|---|---|---|---|
| 5614 | Development of a short form Social Interaction Anxiety (SIAS) and Social Phobia Scale (SPS) using nonparametric item response theory: the SIAS-6 and the SPS-6. | Shortened forms of the Social Interaction Anxiety Scale (SIAS) and the Social Phobia Scale (SPS) were developed using nonparametric item response theory methods. Using data from socially phobic participants enrolled in 5 treatment trials (N = 456), 2 six-item scales (the SIAS-6 and the SPS-6) were developed. The validity of the scores on the SIAS-6 and the SPS-6 was then tested using traditional methods for their convergent validity in an independent clinical sample and a student sample, as well as for their sensitivity to change and diagnostic sensitivity in the clinical sample. The scores on the SIAS-6 and the SPS-6 correlated as well as the scores on the original SIAS and SPS, with scores on measures of related constructs, discriminated well between those with and without a diagnosis of social phobia, providing cutoffs for diagnosis and were as sensitive to measuring change associated with treatment as were the SIAS and SPS. Together, the SIAS-6 and the SPS-6 appear to be an efficient method of measuring | 1 | Development of a short form Social Interaction Anxiety (SIAS) and Social Phobia Scale (SPS) using nonparametric item response theory: the SIAS-6 and the SPS-6. Shortened forms of the Social Interaction Anxiety Scale (SIAS) and the Social Phobia Scale (SPS) were developed using nonparametric item response theory methods. Using data from socially phobic participants enrolled in 5 treatment trials (N = 456), 2 six-item scales (the SIAS-6 and the SPS-6) were developed. The validity of the scores on the SIAS-6 and the SPS-6 was then tested using traditional methods for their convergent validity in an independent clinical sample and a student sample, as well as for their sensitivity to change and diagnostic sensitivity in the clinical sample. The scores on the SIAS-6 and the SPS-6 correlated as well as the scores on the original SIAS and SPS, with scores on measures of related constructs, discriminated well between those with and without a diagnosis of social phobia, providing cutoffs for diagnosis and were as sensitive to measuring change associated with treatment as were the SIAS and SPS. Together, the | development short form social interaction anxiety sias social phobia scale sps use nonparametric item response theory sias sps shorten form social interaction anxiety scale sias social phobia scale sps develop use nonparametric item response theory method use data socially phobic participant enrol treatment trial n six-item scale sias sps developed validity score sias sps test use traditional method convergent validity independent clinical sample student sample well sensitivity change diagnostic sensitivity clinical sample score sias sps correlate well score original sias sps score measure related construct discriminate well without diagnosis social phobia provide cutoff diagnosis sensitive measure change associate treatment sias sps together sias sps appear efficient method measure symptom social phobia provide brief screening tool |

TABLE 1-continued

| S. No | Title | Abstract | COA | Text | Pre-processed text |
|---|---|---|---|---|---|
| | | symptoms of social phobia and provide a brief screening tool. | | SIAS-6 and the SPS-6 appear to be an efficient method of measuring symptoms of social phobia and provide a brief screening tool. | |
| 5616 | The premature infant pain profile-revised (PIPP-R): initial validation and feasibility. | To describe revisions to the Premature Infant Pain Profile (PIPP) and initial construct validation and feasibility of the Premature Infant Pain Profile-Revised (PIPP-R). The PIPP was revised to enhance validity and feasibility. To validate the PIPP-R, data from 2 randomized cross-over studies were utilized to: (1) calculate and compare PIPP and PIPP-R scores in extremely low gestational age infants undergoing a painful and nonpainful event (N = 52; dataset #1) and (2) calculate and compare PIPP and PIPP-R scores in assessing the effectiveness of (a) sucrose, (b) non-nutritive sucking (NNS) + sucrose, and (c) facilitated tucking + NNS + sucrose during heel lance (N = 85; dataset #2). Pearson correlations between PIPP and PIPP-R scores were calculated, and Student t tests and 1-way analysis of variance were used to determine construct validity during painful and nonpainful events. To establish feasibility, a survey of 31 Neonatal Intensive Care Unit nurses was | 1 | The premature infant pain profile-revised (PIPP-R): initial validation and feasibility. To describe revisions to the Premature Infant Pain Profile (PIPP) and initial construct validation and feasibility of the Premature Infant Pain Profile-Revised (PIPP-R). The PIPP was revised to enhance validity and feasibility. To validate the PIPP-R, data from 2 randomized cross-over studies were utilized to: (1) calculate and compare PIPP and PIPP-R scores in extremely low gestational age infants undergoing a painful and nonpainful event (N = 52; dataset #1) and (2) calculate and compare PIPP and PIPP-R scores in assessing the effectiveness of (a) sucrose, (b) non-nutritive sucking (NNS) + sucrose, and (c) facilitated tucking + NNS + sucrose during heel lance (N = 85; dataset #2). Pearson correlations between PIPP and PIPP-R scores were calculated, and Student t tests and 1-way analysis of variance were used to determine construct validity during painful and nonpainful events. To establish feasibility, a survey of 31 Neonatal Intensive Care Unit nurses was conducted. PIPP-R scores were significantly lower during | premature infant pain profile revise pipp r initial validation feasibility describe revision premature infant pain profile pipp initial construct validation feasibility premature infant pain profile revise pipp r pipp revise enhance validity feasibility validate pipp r data randomize cross study utilized calculate compare pipp pipp r score extremely low gestational age infant undergo painful nonpainful event n dataset calculate compare pipp pipp r score assess effectiveness sucrose b non-nutritive suck nns sucrose c facilitate tuck nns sucrose heel lance n dataset pearson correlation pipp pipp r score calculate student test way analysis variance use determine construct validity painful nonpainful event establish feasibility survey neonatal intensive care unit nurse conduct pipp r score significantly low nonpainful mean sd compare painful mean sd p event extremely low gestational age infant dataset dataset pipp r score significantly low infant week gestation group receive nns sucrose compare group f p overall nurse rat pipp r feasible initial construct validation feasibility pipp r demonstrate test infant vary gestational age diagnose pain condition require exploration pipp r relation type physiological cognitive response |

TABLE 1-continued

| S. No | Title | Abstract | COA | Text | Pre-processed text |
|---|---|---|---|---|---|
| | | conducted. PIPP-R scores were significantly lower during nonpainful (mean, 8.3; SD = 2.9) compared with painful (mean, 9.9; SD = 3.1; t95 = 4.51, P = 0.036) events in extremely low gestational age infants in dataset #1. In dataset #2, PIPP-R scores were significantly lower in infants 25 to 41 weeks gestation in the group receiving NNS + sucrose compared with the other 2 groups (F2, 79 = 2.9, P < 0.05). Overall, nurses rated the PIPP-R as feasible. Initial construct validation and feasibility of the PIPP-R was demonstrated. Further testing with infants of varying gestational ages, diagnoses, and pain conditions is required; as is exploration of PIPP-R in relation to other types of physiological and cognitive responses. | | nonpainful (mean, 8.3; SD = 2.9) compared with painful (mean, 9.9; SD = 3.1; t95 = 4.51, P = 0.036) events in extremely low gestational age infants in dataset #1. In dataset #2, PIPP-R scores were significantly lower in infants 25 to 41 weeks gestation in the group receiving NNS + sucrose compared with the other 2 groups (F2, 79 = 2.9, P < 0.05). Overall, nurses rated the PIPP-R as feasible. Initial construct validation and feasibility of the PIPP-R was demonstrated. Further testing with infants of varying gestational ages, diagnoses, and pain conditions is required; as is exploration of PIPP-R in relation to other types of physiological and cognitive responses. | |
| 5637 | Effective continuing education for the busy practitioner. | This paper presents a model for maintaining a program of self-initiated study for the purposes of continuing education in orthodontics. It is suggested that the busy practitioner can gain from a clear perception of the process of learning. | 0 | Effective continuing education for the busy practitioner. This paper presents a model for maintaining a program of self-initiated study for the purposes of continuing education in orthodontics. It is suggested that the busy practitioner can gain from a clear perception of the process of learning. | effective continue education busy practitioner paper present model maintain program self-initiate study purpose continue education orthodontics suggest busy practitioner gain clear perception process learning |

Validation data: An independent validation dataset with 3234 labelled text samples is utilized to check the model's performance. The independent validation dataset reflects the same domain variety as the training set but guarantees no duplication.

In an embodiment, a sample validation data may look like table 2 below:

TABLE 2

| S. No | Title | Abstract | COA | Text | Pre-processed text |
|---|---|---|---|---|---|
| 1 | The assessment of disability with the Groningen Activity Restriction Scale. Conceptual framework and psychometric properties. | The conceptual framework, psychometric properties, descriptive statistics, and the rules for administration and scoring of the Groningen Activity Restriction Scale (GARS) for assessing disability in the area of ADL (Activities of Daily Living including mobility) as well as IADL (Instrumental Activities of Daily Living) are presented. The results show that the GARS, which can be administered both face-to-face and by mail questionnaire, is an easy to administer, comprehensive, reliable, hierarchical, and valid measure for assessing disability in older people. By integrating previously developed scales measuring different domains of disability (ADL, IADL, and mobility) and the use of a four-category response format, an accurate and detailed measure of disability can be obtained and a broader range of needs of subjects can be described. The GARS manual, including detailed procedures for administration and scoring, encourages unambiguous administration and interpretation which results in more comparable research outcomes. | 1 | The assessment of disability with the Groningen Activity Restriction Scale. Conceptual framework and psychometric properties. The conceptual framework, psychometric properties, descriptive statistics, and the rules for administration and scoring of the Groningen Activity Restriction Scale (GARS) for assessing disability in the area of ADL (Activities of Daily Living including mobility) as well as IADL (Instrumental Activities of Daily Living) are presented. The results show that the GARS, which can be administered both face-to-face and by mail questionnaire, is an easy to administer, comprehensive, reliable, hierarchical, and valid measure for assessing disability in older people. By integrating previously developed scales measuring different domains of disability (ADL, IADL, and mobility) and the use of a four-category response format, an accurate and detailed measure of disability can be obtained and a broader range of needs of subjects can be described. The GARS manual, including detailed procedures for administration and scoring, encourages unambiguous administration and interpretation which results in more comparable research outcomes. | assessment disability groningen activity restriction scale conceptual framework psychometric property conceptual framework psychometric property descriptive statistic rule administration score groningen activity restriction scale gar assess disability area adl activity daily live include mobility well iadl instrumental activity daily live present result show gar administer face face mail questionnaire easy administer comprehensive reliable hierarchical valid measure assess disability old people integrate previously develop scale measure different domain disability adl iadl mobility use four-category response format accurate detailed measure disability obtain broad range need subject describe gar manual include detailed procedure administration score encourages unambiguous administration interpretation result comparable research outcome |
| 2 | An overview of the endodontic | This paper seeks to provide the reader with an overview of | 0 | An overview of the endodontic curriculum in Fiji | overview endodontic curriculum fiji |

TABLE 2-continued

| S. No | Title | Abstract | COA | Text | Pre-processed text |
|---|---|---|---|---|---|
| | curriculum in Fiji from 2009 to 2013. | the endodontic curriculum in Fiji from 2009 to 2013. It also intends to inform readers of the changes in endodontic teaching, the learning methods utilized, curriculum development, the transition from block teaching to partial block teaching combined with longitudinal teaching, and the future plans for the endodontic module. | | from 2009 to 2013. This paper seeks to provide the reader with an overview of the endodontic curriculum in Fiji from 2009 to 2013. It also intends to inform readers of the changes in endodontic teaching, the learning methods utilized, curriculum development, the transition from block teaching to partial block teaching combined with longitudinal teaching, and the future plans for the endodontic module. | paper seek provide reader overview endodontic curriculum fiji also intend inform reader change endodontic teach learn method utilized curriculum development transition block teach partial block teaching combine longitudinal teaching future plan endodontic module |

Figure 6A:
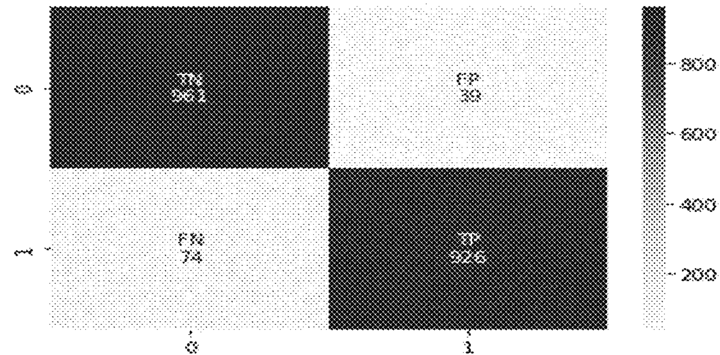
FIG. 6A illustrates the confusion matrix and classification metrics of the Ensemble model when Title is used.
Figure 6B:
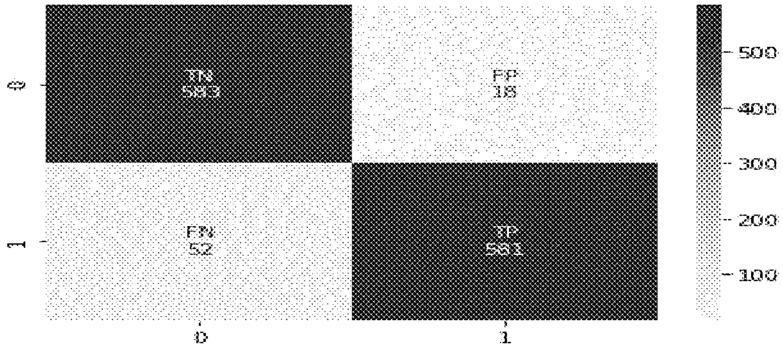
FIG. 6B illustrates the confusion matrix and classification metrics of the Ensemble model when Title is used.

Dataset Characteristics: FIGS. 6A and 6B illustrate the confusion matrix and classification metrics of the Ensemble model when Title is used. The construction of the model starts with using the publication's Title to determine its relevance. Although the Ensemble model using the publication's Title performs quite well, it may overlook certain publications that might be important for development or validation. When relying solely on the Title for classification, the model achieves an overall recall score of about 92%.

Figure 7A:
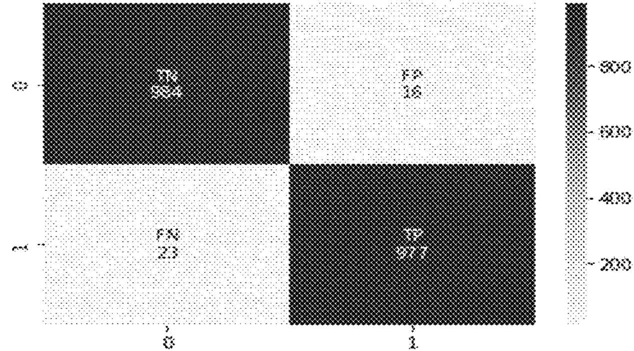
FIG. 7A illustrates the confusion matrix and classification metrics of the Ensemble model when Title and Abstract are used.
Figure 7B:
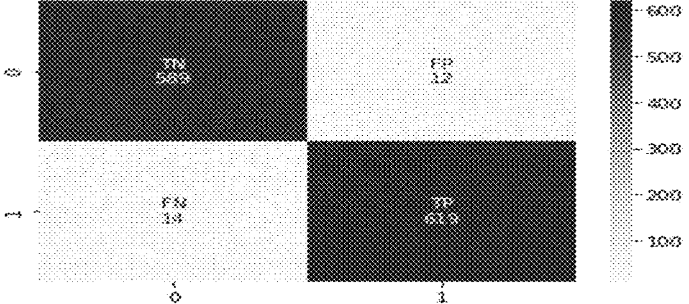
FIG. 7B illustrates the confusion matrix and classification metrics of the Ensemble model when Title and Abstract are used.

FIGS. 7A and 7B illustrate the confusion matrix and classification metrics of the Ensemble model when Title and Abstract are used. In this embodiment, the Abstract alongside the Title may be utilized. The model's recall rate reaches approximately 98% when incorporating both elements, the abstract and title. Since the Title and Abstract are textual data, they are amalgamated into one text field prior to any subsequent analysis.

Data Pre-processing: Being purely textual, distinguishing between positive and negative categories relies on constructing features from the word frequency within the training set. The model's features are crafted through the Term Frequency-Inverse Document Frequency (TF-IDF) technique. It's essential to pre-process the data to remove noise such as stop words, irrelevant symbols, numbers, and Unicode® characters before feature generation.

Step 1: Text Cleaning: This step may include the following points:

- Removal of unwanted characters, such as punctuation marks, digits, and special symbols.
- Converting text to lowercase to ensure uniformity.
- Removal of HTML tags, using regular expressions.
- Removal of all stop words as they may not add significant value to the classification task.

Data cleansing may be performed for preparing raw data for machine learning (ML) and business intelligence (BI) applications. Raw data may contain numerous errors, which can affect the accuracy of ML models and lead to incorrect predictions. Data cleansing may include modifying and removing incorrect and incomplete data fields, identifying and removing duplicate information, and correcting formatting, missing values, and spelling errors.

Step 2: Tokenization: This step includes splitting the cleaned text into individual tokens (words). This step converts the text into a list of words that will be further processed.

Step 3: Text Normalization: This step includes the following points:

- Part-of-Speech (POS) tag may be assigned to each token.
- Applying lemmatization to reduce words to their base or root forms. Lemmatization considers the POS tag assigned to the words and converts them to their meaningful base form.
- Unicode® characters may be standardized by converting them into their closest ASCII representation.

Feature Extraction using TF-IDF: This step further includes the following steps:

In an embodiment, feature vectors may be used to train AI models. Various machine learning techniques and algorithms are applied to build models that can analyze the data and identify patterns, make predictions, and/or classify information. These steps may involve selecting the appropriate algorithms, training the models on the data, and validating their performance to ensure they provide accurate and reliable results.

Step 4: TF-IDF Vectorization: The Term Frequency-Inverse Document Frequency (TF-IDF) technique may be used to convert the text data into numerical feature vectors as the classification model requires the numerical input. This technique is preferred over the other techniques because it provides a weighted score based on the Term Frequency and Inverse Document Frequency.

Term Frequency (TF): This calculates the frequency of each word in the article.

Inverse Document Frequency (IDF): Calculates the importance of each word across all articles in the dataset. Words that are common across many publications are given lower importance, while those unique to fewer publications are given higher importance.

TF and IDF may be combined to produce a weighted score for each word, creating a TF-IDF matrix where each row represents an article, and each column represents a term. By using this technique, the number of features that are generated is 27,334 for the 8000 training samples.

Step 5: Dimensionality Reduction: In an embodiment, in order to reduce the noise and reduce the dimensionality of the TF-IDF matrix, after evaluating with different values of the min_df (minimum number of times a word must appear in the training set to be included in the TF-IDF matrix) for the training sample of 8000 data, based on this embodiment, this value may be chosen as 5. As a result, the feature count gets reduced to 7719 data. To lower the computational demand and choose the crucial features, additional feature selection methods may be utilized. Top features may be chosen using the SelectKBest filter-based feature selection method, which determines the dependency of each feature on the output variable. SelectKBest is a type of filter-based feature selection method where the feature selection process is done independently of any specific machine learning algorithm and relies on statistical measures to score and rank the features. Further, from the 7719 features generated through vectorization, the foremost 2000 are picked via the ANOVA F_classif statistical test. Analysis of Variance (ANOVA) is a statistical formula used to compare variances across the means (or average) of different groups. Since vectorization yields numerical features, the ANOVA F_classif may be a suitable test to identify significant features.

Model Selection and Training: The following steps relate to model selection and training.

Step 6: Data Splitting: The data may be split into training and test, based on the 80:20 ratio, which, in the embodiment, results in 6800 samples used for the training set and 1200 samples for the test set.

Step 7: Classifier Selection: The ensemble model may combine five distinct classifiers: Multinomial Naïve Bayes, Random Forest Classifier, XGBoost, Support Vector Machine (SVM), and Stochastic Gradient Descent (SGD) Classifier. The concept behind this method is that various classifiers possess distinct strengths in detecting and interpreting different aspects of data. Each classifier offers a unique perspective to understanding data characteristics, like feature frequency (Multinomial Naïve Bayes), complex interactions (Random Forest, XGBoost), and linear separability (SVM, SGDClassifier).

Step 8: Model Training: Each of these classifiers in the ensemble model is independently trained on the identical dataset processed through TF-IDF vectorization.

End Conditions: The early stopping criterion is configured in the XGBoost model to determine the optimal number of boosting rounds and prevent overtraining. In an embodiment, the early_stopping_rounds parameter in the XGBoost model is set to 10, and the model in this example identified 408 boosting rounds as optimal based on the training data. The early_stopping_rounds parameter enables early stopping which can help prevent overfitting and save time during training. Similarly, the number of iterations for the SGDClassifier model may be set to 100.

Model Evaluation and Tuning: The following steps may be used for model evaluation and tuning.

Step 9: Model Evaluation: Voting Algorithm: The ensemble model may use a hard voting mechanism, where each classifier in the ensemble makes a prediction, and the final output is determined by a majority vote. The chosen classifiers are diverse in nature, as they approach the problem differently. Multinomial Naïve Bayes handles probabilistic decisions well with text data, while Random Forest captures non-linear interactions. This diversity reduces the risk of overfitting to a particular type of data or noise. Every one of the five classifiers determines a class label for an instance independently (for example, Class 0 or Class 1). The results from each classifier are counted, and the class with the majority votes is selected as the conclusive prediction. To illustrate, if three classifiers vote for Class 1 and two for Class 0, Class 1 will be the ultimate prediction.

Step 10: Hyperparameter Tuning: Hyperparameter tuning is performed using Grid Search technique to optimize the performance of the different classifiers. In an embodiment, the different parameters set for each of the classifiers may be as given below:

- Multinomial Naïve Bayes: The alpha parameter may be set to 0.1 to prevent model overfitting, which results in optimal model performance.
- Random Forest Classifier: Important parameters include n_estimators (how many trees are in the forest), min_samples_leaf (the smallest number of samples necessary at each tree's leaf node), and min_samples_split (the least number of samples needed to divide an internal node). To attain optimal results, these parameters may be configured to 200, 1, and 5, respectively.
- XGBoost Classifier: An early stopping mechanism is used in the XGBoost model to pinpoint the optimal count of boosting rounds and avert overfitting. In an embodiment, with the early_stopping_rounds parameter at 10, the model ascertains that 408 boosting rounds are ideal according to the training set.
- SGDClassifier: Similar to the XGBoost model, SGDClassifier utilizes early stopping with n_iter_no_change set at 10. Through GridSearch optimization, max_iter (the number of iterations) is determined to be 100 and tol (tolerance for the optimization) at 0.001 for optimal model performance. GridSearch is an optimization technique that may be used to find the optimal combination of hyperparameters for a machine learning algorithm.

The machine learning model may be calibrated. Calibration is a comparison of the actual output and the expected output given by a system. Calibration of a machine learning model may involve making little but meaningful changes to the model's predictions in order to improve the accuracy and confidence in those predictions. Calibration is required when making decisions based on probability estimates or gauging the effectiveness of a model. The model may be a self-learning model, that can automatically adapt and improve performance over time based on the feedback it receives from the data and the environment.

Technical solution: The chosen classifiers are linked to technical means by enhancing the model's predictive power and robustness.

- Feature Extraction and Selection: The application layer uses TF-IDF vectorization and filter-based feature selection, ensuring that only the most relevant textual features are processed by the classifiers, optimizing computational efficiency and predictive accuracy.
- SVM and SGDClassifier: These linear models directly map text features (derived via TF-IDF) to the classification output by learning a decision boundary.
- Tree-based Models (Random Forest and XGBoost): These models handle feature interactions automatically, selecting the most relevant features during the training process, which is crucial for handling high-dimensional TF-IDF data.
- Integration of Diverse Algorithms: The ensemble leverages the strengths of various algorithms-probabilistic models (Naive Bayes, SGD with logloss), ensemble trees (Random Forest, XGBoost), margin-based classifiers (SVM)—to create a robust system capable of handling diverse textual data.

Decision Aggregation: The hard voting mechanism serves as a technical means to consolidate individual classifier predictions, enhancing the reliability of the final output.

How Technical Solution is a Technological Advancement:

Technical Contribution: The technical contribution of this invention lies in its innovative approach to binary text classification by integrating multiple classifiers into a robust ensemble model. Each classifier contributes uniquely to capturing different aspects of the data, such as feature frequency (Multinomial Naïve Bayes), complex interactions (Random Forest, XGBoost), and linear separability (SVM, SGDClassifier). The use of TF-IDF vectorization, combined with f_classif feature selection, ensures that the model focuses on the most relevant features, enhancing its predictive accuracy. The application of GridSearchCV (Grid Search Cross-Validation) for hyperparameter tuning further optimizes each classifier, ensuring that the model operates at its best possible performance.

Technical Effect: Empirical evidence from experiments demonstrates that the ensemble model outperforms individual classifiers in terms of accuracy and robustness. Cross-validation results show a significant improvement in prediction accuracy when using the ensemble approach versus any single classifier. The mathematical proof is rooted in the diversity of the classifiers used, each contributing to different aspects of the feature space, thus reducing the overall error rate. By integrating classifiers with diverse inductive biases and learning mechanisms, the ensemble mitigates individual weaknesses, capitalizing on the principle that collective decisions often surpass solitary judgments.

Figure 8:
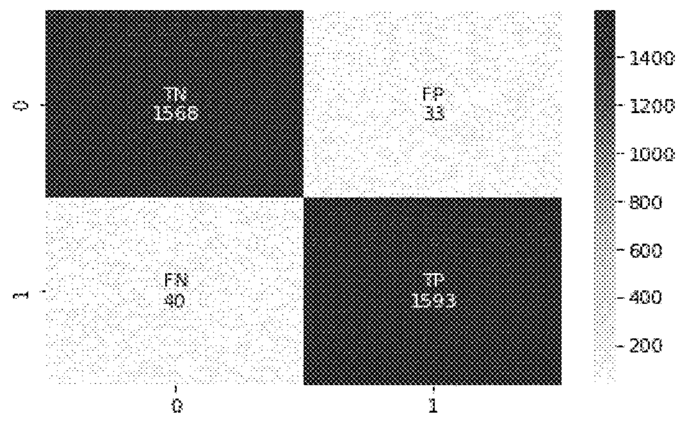
FIG. 8 illustrates the confusion matrix and classification metrics of the Ensemble model for the validation dataset according to an embodiment.

FIG. 8 illustrates the confusion matrix and classification metrics of the Ensemble model for the validation dataset according to an embodiment. Validation on unseen data showcasing the model's generalizability, with performance metrics such as accuracy, precision, recall, and F1-score reflecting significant improvements over baseline models.

Human Inputs:

Model Architecture: The classifiers may be selected and configured based on prior domain knowledge and empirical testing to form the ensemble, ensuring coverage of various analytical perspectives.

Feature Engineering: The decision to use TF-IDF vectorization with a min_df of 5 and selecting the top 2,000 features using 'f_classif is driven by domain expertise, balancing feature richness with noise reduction.

Improving Training Algorithms: GridSearchCV is meticulously used to fine-tune model parameters, requiring informed decisions regarding parameter ranges and evaluation metrics. For instance, Adjustments are made to the training algorithms, such as using early stopping in XGBoost and tuning learning rates in SGDClassifier to optimize convergence rates and prevent overfitting.

Filtering Training Data: Pre-processing steps, such as stop word removal and lemmatization, and feature selection are iteratively done based on domain expertise to ensure that the text data provided meaningful input to the models.

Figure 9:
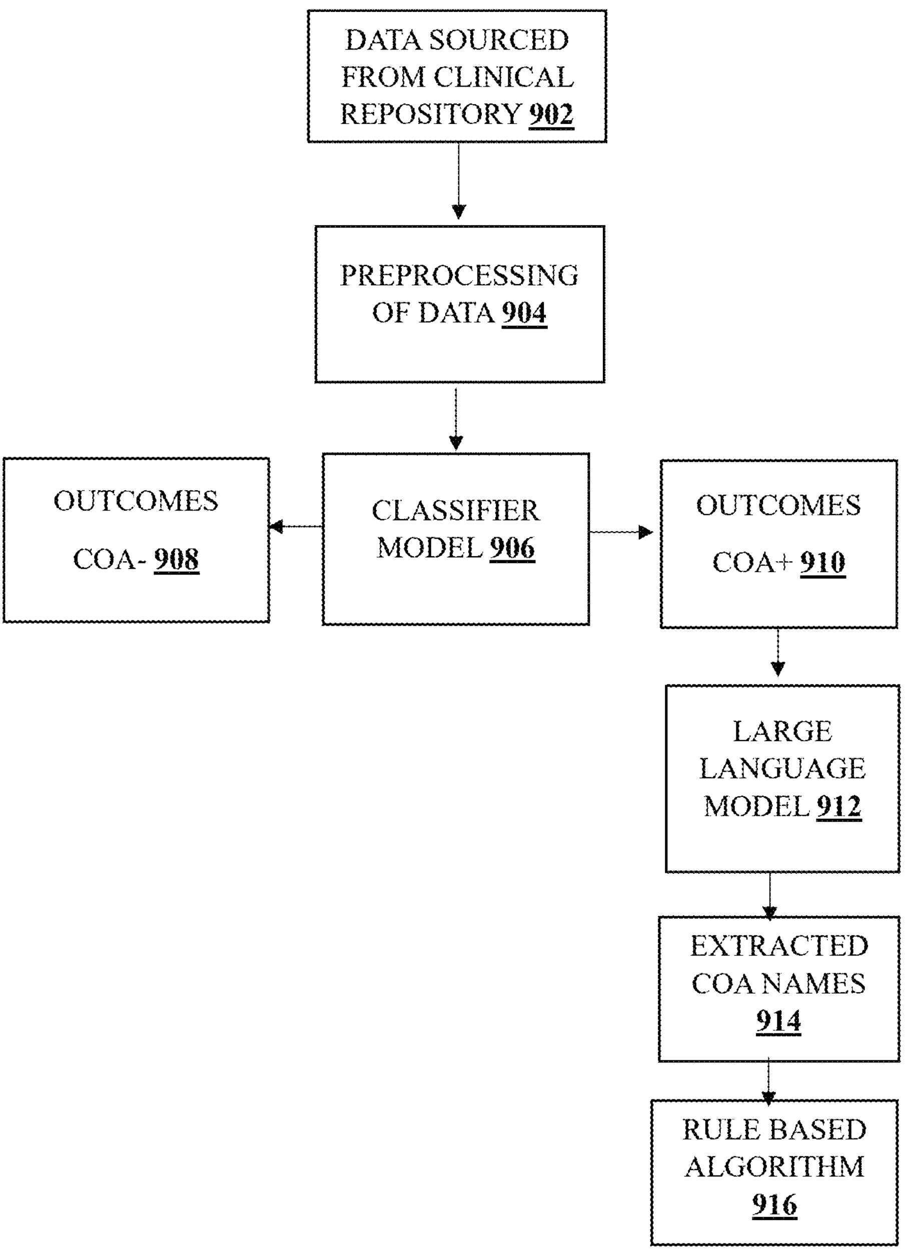
FIG. 9 illustrates a clinical repository AI assisted COA data curation according to an embodiment.

FIG. 9 illustrates a COA data curation pipeline for a clinical repository. Each step ensures the models are well-trained and capable of providing valuable outputs. This systematic approach ensures that the AI models are robust, accurate, and effective in addressing the specific problems they are designed to solve. As it is crucial for sponsors to evaluate which COAs have been used in clinical studies to build their COA strategy, sponsors have to be able to quickly identify COA names in clinical repositories outcome descriptions.

At step 902, data may be sourced from the clinical repository. The data is extracted from a clinical repository using either the repository Application programming interface (API), clinical repository database or the clinical repository website data export feature. All trials and attributes are extracted. For example, for extracting data from the Clinicaltrials.gov (CT.gov) repository, one of the following may be used CT.gov API, Aggregated Analysis of ClinicalTrials.gov (AACT) Database that contains all information (protocol and result data elements) about every study registered in ClinicalTrials.gov, or CT.gov website comma-separated values (CSV) export feature. The Study ID, Outcome type, Outcome measure and Outcome description may initially be extracted from the ClinicalTrials. gov using an API. At step 904, the gathered data may be subjected to the required pre-processing, which encompasses feature selection. At step 906, the classifier model may receive the pre-processed outcome measure and description of the study as input. The system may triage clinical repository outcomes containing COAs using a classifier model. Each individual clinical trial can have multiple outcomes describing clinical endpoints. Each outcome can either contain the description of a COA or not. To restrict the number of outcomes needed to be screened to extract COA names, a classifier model has been developed. The classifier model gives the probability of each clinical repository outcome to mention a COA or not. At step 908, the classifier model gives the probability of each clinical repository outcome that does not mention a COA. At step 910, the classifier model gives the probability of each clinical repository outcome that mentions a COA. The classes containing a COA may be represented as COA+ classes, and the classes without a COA may be represented as COA−classes. In an embodiment, the classifier may determine if the outcome has a presence of COA in it or not and will show a 1 or 0, with 1 indicating that it has a COA, and 0 indicating it does not have a COA (classification result). At step 912, the system may extract COA names from the clinical repository outcomes using a Large Language Model (LLM). The clinical repository outcomes identified as describing COAs (COA+) by the classifier model in step 910 are fed to a Large Language Model that extracts COA names from the clinical repository outcome text (outcome title and/or description). The triage step using the classifier may considerably reduce the amount of input data fed to the LLM. In an embodiment, the outcomes categorized under class 1 may have their Outcome measure and description processed by the LLM model, which is tasked with identifying the names of COAs present within these texts. At step 914, the resulting output may consist of the extracted COA names. At step 916, the system may utilize a rule-based algorithm to reconcile and harmonize COA names. The COA name generated may be input into the algorithm to determine if it matches any existing COAs in the database and to assign a similarity score. COA names may be described in many ways and spellings by different researchers in a clinical repository. To analyze COA-related information, data needs to be reconciled for the same or similar COA across trials and outcomes. The system utilizes a rule-based algorithm using Natural Language Processing (NLP) developed to reconcile the COA names found in clinical repositories with standard naming convention or ontology. For example, the COA names may be reconciled using PROQOLID database. PROQOLID is the largest and unique COA information database maintained by Mapi Research Trust, which lists 6000+COAs.

The final step involves deploying the trained AI models for practical use. These models are applied to new, unseen data to make predictions, provide insights, or assist in decision-making processes. The models can be integrated into systems where they continuously process incoming data and generate outputs that support various applications, such as determination of COA in a clinical repository or a scientific publication. The model may be a self-learning model that based on the data, training, and feedback adjusts itself accordingly.

Figure 10:
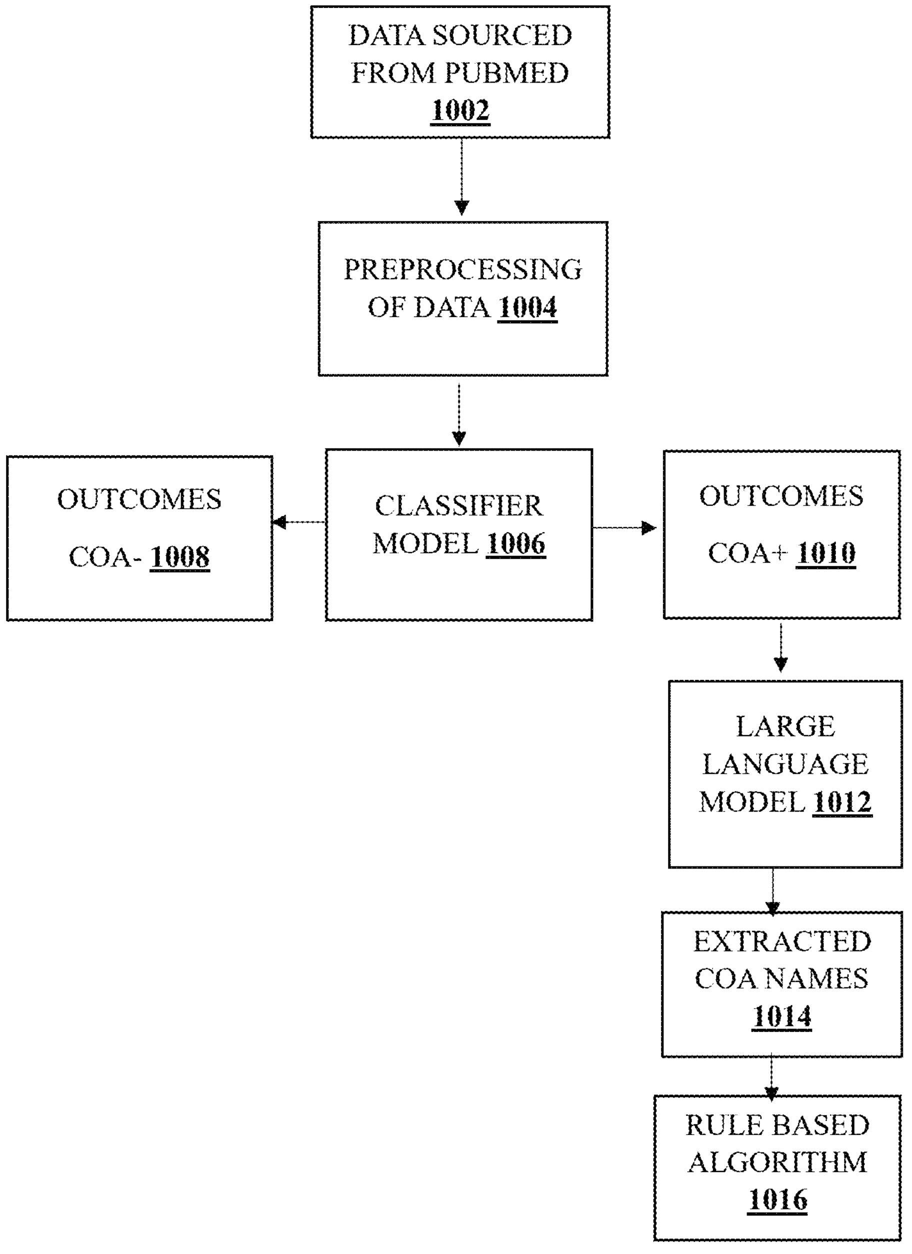
FIG. 10 illustrates a scientific publication AI assisted COA data curation according to an embodiment.

FIG. 10 illustrates a COA data curation pipeline for a scientific publication. It is crucial for sponsors to obtain information on the evidence supporting the development and validation of COAs, to evaluate which COAs are fit-for-purpose for their study. At step 1002, the Data may be sourced from scientific publications, for example PubMed. Data may be extracted from the scientific publication API. In the case of PubMed, the data may be extracted from PubMed API (Entrez): PubMed titles, abstracts, and metadata. The Publication ID, PMID (PubMed ID), article title, and abstract may initially be extracted from the PubMed database using an API. At step 1004, the gathered data may be subject to the required pre-processing, which encompasses feature selection. At step 1006, the system may triage PubMed abstracts describing COA development and validation using a classifier model. The Classifier model receives the processed title and abstract of the publications as input. This information is available in "COA development and validation publications" in PubMed. COA development and validation publications represent an estimated 1% of PubMed publications. It is manually very challenging and time-consuming to pinpoint these publications, as keyword based strategies are either too specific or too sensitive. To restrict the number of scientific publications needed to be screened to extract COA information and to reduce the risk of missing publications due to a specific keyword based strategy, a classifier model has been developed. The classifier model gives the probability of each scientific publication record to be a COA development/validation publication or not. At step 1008, the classifier model gives the probability of each scientific publication that does not mention a COA. At step 1010, the classifier model gives the probability of each scientific publication that mentions a COA. The classes containing a COA may be represented as COA+classes, and the classes without a COA may be represented as COA− classes. In an embodiment, the classifier may determine if the publication is for development or validation and will show a 1 or 0, with 1 indicating that it is a development/validation publication, and 0 indicating it is not. At step 1012, the system may extract COA names from scientific publication abstracts using a Large Language Model (LLM). Scientific publication abstracts identified as describing COA development/validation studies (COA+) by the classifier in step 1010 are fed to a Large Language Model that extracts COA names from scientific publication title/abstract text. In an embodiment, publications categorized under class 1 may have their title and abstract processed by the LLM model, which is tasked with identifying the names of COAs present within these texts. At step 1014, the resulting output may consist of the extracted COA names. Having triaged the scientific publication abstracts with a classifier, this considerably reduces the amount of pre-processed input data fed to the LLM. At step 1016, the system may utilize a rule-based algorithm to reconcile COA names extracted by the LLM. The COA name generated is input into the algorithm to determine if it matches any existing COAs in the database and to assign a similarity score. The resulting output may consist of the extracted COA names. COA names can be described in many different manners and spellings by researchers in the text of scientific publications. To analyze COA information, data needs to be reconciled for the same COA. The system utilizes a rule-based algorithm using Natural Language Processing (NLP), developed to reconcile the COA names found in scientific publications standard COA naming convention or ontology. For example, the COA names may be reconciled using the PROQOLID database.

The result that the business will review, in an embodiment, may look like table 3 below:

TABLE 3

| PubMed ID | Title | Abstract | Classification Result | LLM Results | Similar COA |
|---|---|---|---|---|---|
| 25181605 | Further development in the assessment of psychological flexibility: a shortened Committed Action Questionnaire (CAQ-8). | Committed action is a relatively understudied facet of the psychological flexibility model but a potentially important process of overt behavior in relation to chronic pain. In this study, we take a previously developed measure of committed action, the Committed Action Questionnaire (CAQ), and validate a shorter version. A total of 664 adults seeking treatment for chronic pain participated in this study. They provided responses to the CAQ and also completed measures of acceptance and health-related daily functioning. Exploratory and confirmatory factor analyses as well as Mokken scaling analysis were used to explore the structure of the CAQ and produce an 8-item version (CAQ-8). A two-factor scale emerged from the analyses that both meet criteria for reliability and validity and performs | 1 | COA's available: Committed Action Questionnaire - 8 items | [{Community integration Questionnaire: 81, Committed Action Questionnaire-8: 100, Committed Action Questionnaire: 97}] |

TABLE 3-continued

| PubMed ID | Title | Abstract | Classification Result | LLM Results | Similar COA |
|---|---|---|---|---|---|
| | | comparably to the longer original version. In validity correlation analyses, committed action as measured by the CAQ-8 was significantly associated with pain related and general acceptance and with depression, physical and social functioning, mental health, vitality, and general health. The CAQ-8 appears equally adequate as the CAQ as a measure of committed action. Its development ought to facilitate further study of this process of engagement in activity and of the wider psychological flexibility model in relation to chronic pain. | | | |

In an embodiment, the integrated data curation pipeline uses different machine learning techniques together to extract COA names from CT.gov and PubMed in an efficient manner for users, as they are integrated as an end-to-end solution. The classifier models are unique machine learning models trained on domain specific data and expertise. The classifier model may be a self-learning model that automatically learns and improves its performance based on the feedback received from the data and environment. The rule-based NLP algorithm can harmonize COA names from CT.gov and PubMed publications to COA names from the COA naming standards.

This tackles the challenge of reconciling the data for the same COAs that are heterogeneously named across different data sources. The fine-tuned LLM model is trained specifically to recognize COA names based on domain specific data and expertise. The manner in which the system is arranged and implemented into a data curation pipeline is efficient and usable by end-users and is impossible to achieve in other ways. The LLM is integrated in a pipeline designed based on domain expertise and accompanied by classifiers and rule-based algorithms that manipulate the data to optimize the result of the LLM. The LLM model may be a self-learning model. The system may provide automatic extraction and harmonization of COA names from text obtained from different sources with the ability to analyze associated data in one solution.

Technical specifications of an example model: Classifiers:

Two machine learning classifier models may be built, one for ClinicalTrials.gov (CT.gov), CT.gov classifier, and another for PubMed abstracts, PubMed classifier. OCT.gov classifier: discriminates between CT.gov outcomes that contain COA(s) versus outcomes that do not contain COA(s) (COA+vs COA−).

PubMed classifier: discriminates between COA development-validation publications and other publications (COA+vs COA−).

Supervised learning: classifier models are trained on balanced datasets manually reviewed:

CT.gov training dataset: N-6000 manually reviewed CT.gov outcomes that contain 50/50 positive/negative class.

PubMed training dataset: combination of N=4000 positive and N=4000 negative classes.

Positive class sample: titles and abstracts of PubMed references linked to COAs in an existing database, PROQOLID.

Negative class sample: PubMed titles and abstracts randomly selected across seven 5-year time periods from 1990-2023 and that do not mention COA names (according to NLP rule-based algorithm comparing CT.gov text with COA names in existing database).

Training datasets may be cleaned (removing special characters and stop words) and transformed into a matrix of TF-IDF features. The top 2000 (PubMed) and 1500 (CT.gov) most frequent features may be selected to build a classifier model. This process is carried out to avoid high cost and difficulty in sending large amounts of data to LLM for processing. Further, feature selection and classifier combination may help improve citation filtering accuracy. Using a classifier model helps to filter potential information and send only relevant information to LLM for extraction, thus reducing cost and improving accuracy.

As mentioned above, the model may be built based as an ensemble model combining five different models to discriminate between positive or negative classes: Random Forest classifier, XGBoost, Support Vector, Stochastic Gradient Descent, Logistic Regression. The final rule is a hard Voting algorithm which results in tallying up the predictions made by all five base models and selecting the class. A threshold of 50% may be chosen to discriminate between classes.

Classifier models may be validated using balanced datasets of N=1000 records for CTgov and N=2000 for PubMed. For CTgov, an imbalanced dataset may also be tested to reflect real-life use.

Logistic Regression model is ideal for binary classification problems, making it suitable for predicting the likelihood of presence of clinical outcome assessment in a clinical outcome. By analyzing the relationship between multiple independent variables (e.g., each individual clinical trial can have multiple outcomes describing clinical endpoints) and the binary outcome (each outcome can either contain the description of a COA or not), logistic regression can estimate the probability of presence of a COA.

Support Vector Machines (SVM) models are effective in high-dimensional spaces and are used for both classification and regression tasks. For COA tracking prediction, SVMs help classify clinical repositories and scientific publications into different probability categories based on certain keywords. By finding the optimal hyperplane that separates the data into different classes, SVMs can accurately predict the likelihood of an outcome to mention a COA.

In an embodiment, ensemble methods may be used. Ensemble methods combine the predictions of multiple models to improve accuracy and robustness. Examples include Random Forests and Gradient Boosting Machines (GBM). By aggregating the predictions of several decision trees (as in Random Forests) or sequentially improving the model (as in GBM), ensemble methods enhance predictive performance and reduce the risk of overfitting. For COA prediction, ensemble methods provide a more comprehensive assessment by leveraging the strengths of different models. In an embodiment, each method can provide various outputs and each method, and each output of the method, can be weighted before the results are assembled into one single prediction result for each prediction.

In an embodiment, various ensemble methods used include bagging, boosting, stacking, voting, and blending. Bagging, exemplified by Random Forest, involves training multiple instances of the same model on different subsets of the training data and combining their predictions. Boosting, used in algorithms like AdaBoost and XGBoost, sequentially builds models that correct the errors of their predecessors, with final predictions being a weighted combination of all models. Stacking performs training of multiple base models, using their predictions as inputs to a higher-level meta-model for the final prediction. Voting combines predictions from multiple models by majority vote or averaging. Blending, similar to stacking but simpler, uses a holdout validation set for training the meta-model. These ensemble methods are powerful tools for reducing overfitting and variance, leading to better generalization on unseen data and improving predictive performance in both competitions and real world applications. These models are integrated, and the AI system can provide assessments for COA tracking, enabling clinical trial sponsors to implement targeted and personalized COA strategy design.

Fine-tune Large Language Models (LLM)

- LLM may be used for information extraction from scientific papers with feature selection and classifier combination.
- The Google foundation model text-bison@002 may be used to extract COA names from CT.gov and PubMed text:
  - OCT. gov LLM: used with 1-shot prompt.
  - PubMed LLM: fine-tuned with a training dataset.
- Supervised tuning technique may be used to train PubMed LLM:
  - The PubMed LLM may be trained using a dataset of 831 manually labelled examples. The examples comprise the PubMed title and abstract (input) and the respective COA name manually extracted from the title and abstract (desired output).
  - The 831 PubMed references may be selected from the existing database as related to visible COA pages, PROs (patient-reported outcomes) and may be manually reviewed: each PubMed title or abstract has to mention the COA acronym or full name in the text, and each PubMed record has to be an original development or validation publication of the COA.

Each training example may be passed to the model in the following format:

Prompt:

{"input_text": "CONTEXT: Extract the COA names mentioned in the TITLE and ABSTRACT. A COA is a measure that describes or reflects how a patient feels, functions, or survives. It can be in the form of a questionnaire or assessment or instrument or tool or form or score or scale or index or rating.

\nTITLE: The development of the Herpes Symptom Checklist and the Herpes Outbreak Impact Questionnaire \nABSTRACT: To develop measures of the day-to-day symptomatic and functional impact of recurrent genital herpes (RGH) outbreaks. The Herpes Outbreak Impact Questionnaire (HOIQ) and the Herpes Symptom Checklist (HSC) were designed to be acceptable to clinical professionals and to reflect patients' experience. Scale content was derived via literature review and interviews with RGH patients and physicians. Questionnaires were assessed for face/content validity in the UK and the language checked for acceptability in the United States. The US measures were assessed for face/content validity with patients. Scaling/psychometric properties were determined via web survey. Participants completed the questionnaires twice during an outbreak, with 24 to 72 hours between administrations. Respondents found the questionnaires relevant and easy to understand and complete. Application of Rasch analysis resulted in the removal of two HOIQ items. Both scales were found to be unidimensional. Item stability testing for the HOIQ indicated that the measure is reproducible. Internal consistency was good (alpha: time 1=0.87, time 2=0.91). Discriminative validity was demonstrated by the measure's ability to distinguish between individuals who differed by self-reported severity of outbreak. The HOIQ and HSC were both responsive to change over time. The HSC and the HOIQ can determine the impact of a herpes outbreak effectively. They are designed to be used daily during such outbreaks and to determine the effectiveness of RGH treatment.", "output_text": "COA's Available: Herpes Outbreak Impact Questionnaire; Herpes Symptom Checklist"}

Representation Learning: Performance of the prediction model depends upon the quality of data pooled for training the model. Deep neural network models are trained to learn data representation for the data considered as the input. To improve the performance of the prediction model, vector representation can be adopted to denote the content in the clinical trial. Furthermore, information extracted from the various sources of data is also combined with the other characteristics of the data and are represented as vectors.

Learning & Extracting from Text Data: The AI suite of the system has neural network models of type recurrent neural networks to perform the task of extracting information from the unstructured data such as lab reports, staff's notes, etc. Models can be trained to identify the clinical concepts in text and map them to the standard clinical approaches. Thereby trained models enable transformation of unstructured text into information represented in vectors.

Learning & Extracting from Image Data: The AI suite of the system comprises deep neural network models of type convolutional neural networks to perform the extraction of information from different types of scans such as ultrasound, Magnetic Resonance Imaging (MRI) etc. Networks are trained to learn object segmentation from the scanned images. Once trained, the model has the ability to detect objects from the knowledge it has gained about image features. Upon extraction of the object from the scanned image, information about the properties of the object is represented in vectors.

Information extracted from deep neural networks can then be passed to the stacked neural networks with deep hidden layers. These layers have a large number of nodes with non-linear activation functions and thus have the ability to capture the non-linear association with the various data characteristics of the COA tracking. Projection of the risk element characteristics to the higher dimension will enhance the opportunity to better understand the association between different characteristics. Training of the model is done in the context of supervised learning. Consequently, the model's ability to identify and extract patterns from the COA characteristics pertaining to a domain specific COA can be reliable with statistical significance. Further, training of the entire stacked deep network can be repeated to identify optimal values of epochs and batch size.

In an embodiment, the AI model used for ascertaining the occurrence of COA may use Bayesian Network. The Bayesian network uses probability theory for prediction and provides decision-making under uncertain conditions such as the ones that may arise during the course of a COA determination. The Bayesian network uses nodes and arcs as in the decision trees algorithm, for providing predictive analytics and identifying patterns thereby enabling occurrence of COA probability decisions.

In an embodiment, the AI model may use a sparse neural network for the assessment of occurrence of a COA. As this model focuses on the most relevant parameters and components, it provides for reduced computations and less memory usage while the efficiency is enhanced. By using this model, the risk factors that mainly affect the outcome may be considered for determination of occurrence of COA. Sparse models may use lasso technique for identification of the relevant features that can impact the outcome. Sparse models may also provide interpretability as the relevant features are selected from the entire dataset, in order to predict the occurrence of COA.

Techniques such as dropout and regularization can be utilized to reduce the bias in the model's prediction and increase its capability to generalize knowledge from the various characteristics to predict the determination of a COA. Further, the model's hyper parameters such as depth of the network, dimensions, learning rate and momentum can be fine-tuned to improve the power of predictability of occurrence and determination of COA by leveraging the optimization techniques including, but not limited to, gradient descent, stochastic gradient descent, and their flavors (speed, memory, noise).

Risk Stratification and Insight Delivery: To increase the viability of a COA interpretation, the prediction results can be stratified into Low, Medium, and High. This is done by the system by using modules of statistical techniques to perform operations such as normalization, standardization of predicted values and identification of thresholds to classify a COA occurrence probability as low, medium, and high. Such a classification of COA determination, in various embodiments, can help in easy assessment and interpretation of the determination of COA.

Feedback layer: In addition, the system also provides its algorithms the self-learning capabilities to learn continuously from the data provided. Such an ability in various embodiments can be potentially useful in identifying and designing optimal COA tracking strategies. The feedback layer provides continuous feedback to the model making it possible to self-learn.

The system includes in various embodiments of the claimed invention an AI suite which executes multiple machine learning models to find the optimum model yielding highest metrics of evaluation. The AI suite includes, but is not limited to, models as simple as logistic regression, and Support Vector Machine (SVM) regression to complex models such as neural networks including, but is not limited to, convolutional neural network (CNN), recurrent neural network (RNN) and long short-term memory model (LSTM).

In one possible configuration of the system, all available types of pre-processed input data can be used to train multiple models, and the best model may be used for predicting the occurrence of COAs in clinical repositories and scientific publications.

In another possible configuration of the system, multiple machine learning models may be trained on a subset of data and the best ensemble of those models may be used for the prediction in various embodiments of the claimed disclosure. For example, CNN models may be trained using image scans data, RNN models may be trained using clinical trial data and medical history data and so on. Then best performing models from each input data type may be assessed for concordance among them and then all those models may be ensembled or stacked together to predict the occurrence of COA in a clinical repository or a scientific publication.

The system not only uses the structured data fields like age, race, but may also use unstructured data from sources like patient reports, audio, and video files of patient encounters. It may use a comprehensive list of data fields which include demographic information, clinical data (e.g., patient history), laboratory tests, investigational biomarkers, genetic testing, microbiome, imaging studies (esp. ultrasound), medications, clinical notes—by physicians, nurses, site staff, nutritional data, patient experience scores, institutional data—to investigate the impact of practice patterns, physician data (for examining the impact of individual providers on outcome) and audio/video files of Clinician-patient Interactions. The models leverage advanced computing capabilities and are not limited to: Artificial Intelligence (including neural networks, Natural Language Processing and understanding, deep learning) and traditional statistical techniques; and can analyze structured and unstructured datasets including, but not limited to: biomarkers and biochemistry data, images, genetics, clinician notes, audios and videos, demographic and socio-economic data, clinical trial data and scientific publications data. The system may continuously receive real-time feedback and accordingly improvise COA tracking on a perpetual basis. It leverages cutting-edge computing capabilities of AI, Mathematics and Statistics, analyzes relevant data (e.g., genetics, images, clinician's notes, audio and videos, healthcare records, wearable devices, pathology etc.) and generates unparalleled results in tracking clinical outcome assessments.

Figure 11:
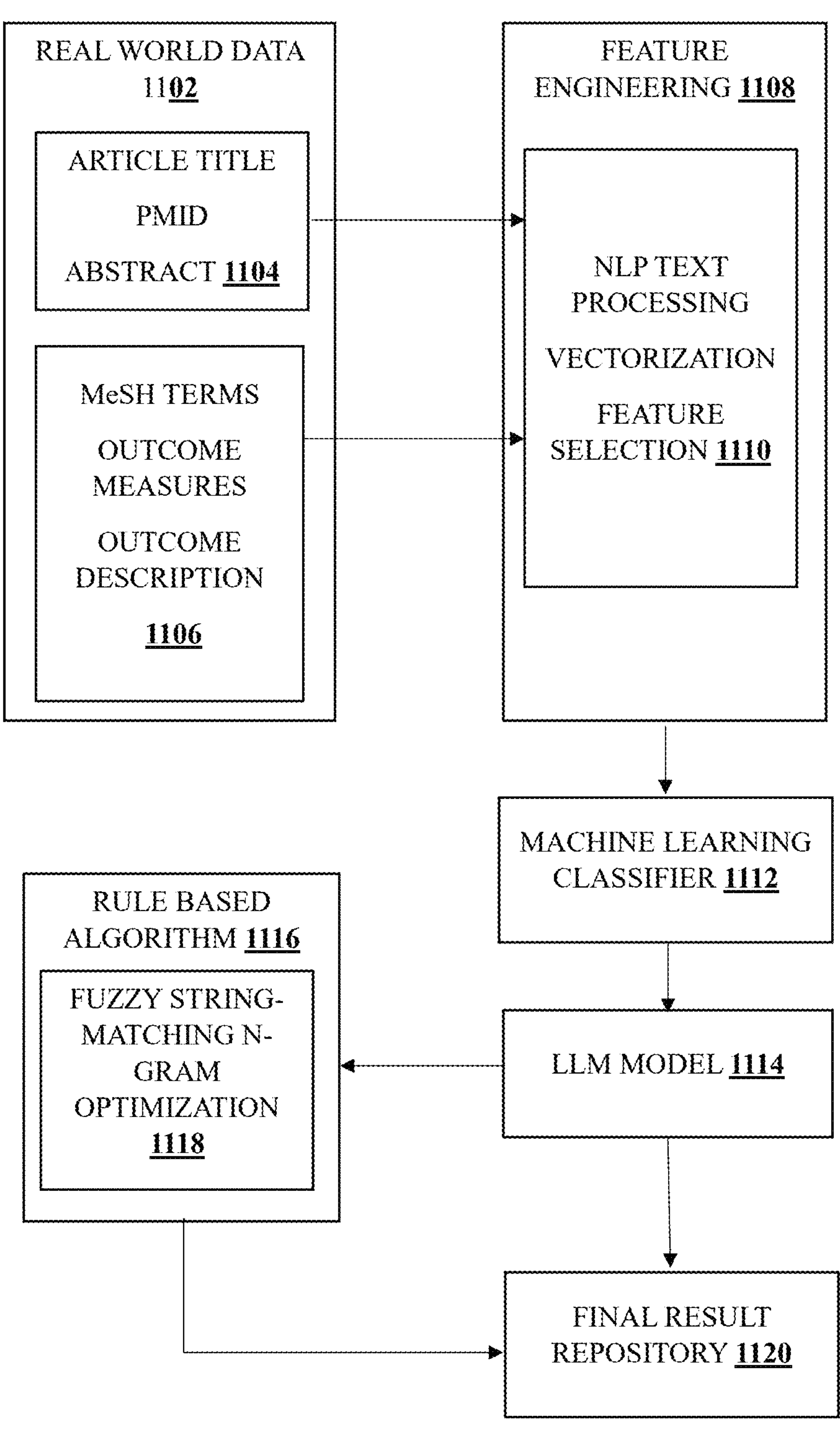
FIG. 11 illustrates NLP components used according to an embodiment.

FIG. 11 illustrates NLP components used, according to an embodiment.

Real world data 1102 may include article title, PMID, and abstract 1104. Real world data may further include MeSH terms (Medical Subject Headings), outcome measures, and outcome description 1106. MeSH is a comprehensive controlled vocabulary thesaurus used for indexing articles, journal articles, and books in the life sciences. The real world data may be transferred to feature engineering 1108. Feature engineering is a pre-processing step in supervised machine learning and statistical modeling which transforms raw data into a more effective set of inputs, each input comprising several attributes, known as features. Feature engineering may include NLP text processing, vectorization, and feature selection 1110. Vectorization is a method that may be used to convert text data into numerical representation for the machine learning algorithm to understand and process. The output of feature engineering may be transferred to machine learning classifier model 1112. The output of the machine learning classifier model 1112 may be input to LLM model 1114. COA names may be extracted by the LLM model and input to the rule-based algorithm 1116. The rule-based algorithm may include fuzzy string matching n-gram optimization 1118. An n-gram is a collection of n successive items in a text document that may include words, keywords, numbers, symbols, letters, syllables, etc., used to understand the search terms, optimize the keywords, capture information about the structure of words and phrases in a text dataset, and where sequences of words are relevant. The output of the rule-based algorithm may be output to the final result repository 1120. The details follow in the following paragraphs.

Rule-based algorithms: COA names can be described in many ways and spellings by different researchers in different clinical repositories, such as in CT.gov, and scientific publications. To analyze COA-related information, data needs to be reconciled for the same COA across trials and outcomes. A rule-based algorithm using Natural Language Processing (NLP) has been developed to reconcile the COA names found in clinical repositories and scientific publications with existing COA names in existing databases.

A rule-based algorithm is built using Natural Language Processing (NLP) to reconcile COA names extracted from clinical repositories and scientific publications text to COA names from the COA acronym database.

Rules may be determined based on human logic and expertise to recognize COA names in clinical repositories and scientific publications outcome text and may be derived into an algorithm using Python Fuzz library and levenshtein distance. Different thresholds for comparing the similarity between clinical repositories and scientific publications COA and existing COA names may be tested between 70-100%. It may be decided to accept a final threshold of 85%-100% for satisfactory accuracy/precision/recall.

Dataset Characteristics: To pinpoint the COAs in a clinical study, the essential data characteristics for creating an algorithm may include the study's outcome measure, outcome description, conditions, and mesh terms.

In an embodiment, these data extracted from a data source may look like table 4 below:

TABLE 4

| NCT ID | MESH _TERMS | CONDITIONS | Outcome type | OUTCOME |
|---|---|---|---|---|
| NCT02129751 | Depressive Disorder Depression Depressive Disorder Major | Major Depressive Disorder | primary outcomes | Mean change from Baseline to EOT in total CDRS-R (raw) score \| Change from Baseline to EOT in total Children's Depression Rating Scale - Revised (CDRS-R). A higher score indicates a more profound state of depression. The interviewer rates 17 symptom areas; the symptom scores are summed to generate a total score. The total score ranges from 17 to 108. |
| NCT03070132 | Trigeminal Neuralgia Neuralgia | Trigeminal Neuralgia | secondary outcomes | Change From Baseline in the Penn Facial Pain Scale-Revised (PENN-FPS-R) Score by Visit During the Long Term Extension (LTE) Period \| The Penn-FPS-R is a new 12-item Health-Related Quality of Life outcome measure with content validity that can be used to assess and monitor the impact of Trigeminal Neuralgia and facial pain treatment interventions in both clinical practice and research. This scale uses the 0-10 numeric rating scale (NRS) to quantify the pain impact different activities and quality of life items, where 0 indicates no interference and 10 indicates complete interference. The sum of the rated NRS score will be calculated. |
| NCT02928094 | Angina Pectoris Myocardial Ischemia Coronary Artery Disease Angina Stable Ischemia | Angina Stable | secondary outcomes | Change in quality of life \| Seattle Angina Questionnaire |
| NCT03463954 | Neoplasms Breast Neoplasms | Malignant Neoplasm of Breast | secondary outcomes | Health-related quality of life outcome measures at three timepoints via EORTC QLQ-C30 & QLQ-BR23 questionnaire (baseline and 4-6 weeks post-laser ablation and post-surgery) \| Health-related quality of life outcome measures |

Given that COA names may appear in either the Outcome measure or its description, these features are combined into a single Outcome column. The combined Outcome field becomes the main textual resource for identifying COAs, with additional features serving to corroborate that the COAs have been accurately pinpointed. The required COAs may be identified using an existing database, which may be a well-maintained resource, listing all current market COAs.

In an embodiment, the sample of existing database data may look like table 5 below:

TABLE 5

| ID | Acronym | Full name | Authors | Therapeutic indications | Number of items |
|---|---|---|---|---|---|
| 1 | EoE-SQ | Eosinophilic Esophagitis - Symptom Questionnaire | Dellon ES \| Rothenberg M \| Hirano I \| Chehade M \| Bredenoord AJ \| Spergel J \| Zhao Q \| Beazley B \| Guillemin I \| Mannent L \| Laws E \| Amin N \| Shumel B \| Maloney J \| Kamat S | Eosinophilic Esophagitis | 5 |
| 2 | EORTC QLQ-H&N35 | EORTC Quality of life - Head and Neck Cancer Module | EORTC Quality of Life Group | Head and Neck Neoplasms | 35 items |
| 3 | Family Star | Family Star | MacKeith J | Non-disease specific | |
| 4 | ACHD PRO | Adults with Congenital Heart Disease Patient-Reported Outcome | Cedars AM \| Ko JM \| John AS \| Vittengl J \| Stefanescu-Schmidt AC \| Jarrett RB \| Kutty S \| Spertus JA | Heart Defects, Congenital | |
| 5 | HFB | Haemangioma Family Burden questionnaire | Boccara O \| Méni C \| Léauté-Labreze C \| Bodemer C \| Voisard JJ \| Dufresne H \| Brauchoux S \| Taïeb C | Non-disease specific | 20 |

Features such as the COA's full name, acronym, therapeutic indications, author, and item count may be utilized to pinpoint COAs in a clinical study. The dataset may include various formats, abbreviations, and possible acronym patterns. The dataset may also contain a few hundred COA names and their variants for comprehensive testing of the algorithm's matching efficiency.

Data Pre-processing: Cleaning COA database features may include the following steps:

Removal of the Copyright, Trademark and Registered symbols from the Acronym and the Full name.

Identification and removal of the most common words among the Therapeutic Indication feature using the word cloud across all the COAs. In an embodiment, this included the removal of 320 most generic words (disease, disorder, etc.) from 1157 unique words. Words removed may be manually verified by the business team.

The other symbols are replaced with a space character.

Author initials may be removed, and the first name of the author may be retained.

Extracting Clinical Study Outcome Features:

The possible Acronym patterns from the outcome text may be extracted using the regular expression patterns.

Similarly, the number of items of the COA mentioned in the text may also be extracted using regular expression patterns.

Selection of the string matching methods: The algorithm may provide an advanced text matching algorithm designed to accurately identify and verify existing COA names within a text data source. The algorithm may utilize both acronym matching and fuzzy string matching techniques, supplemented by comparisons of additional features such as therapeutic indications, number of items in the COAs, and author names. The algorithm may leverage the Fuzz library in Python, utilizing methods such as ratio( ) partial_ratio( ) and token_set_ratio( ) to compute similarity scores between input text and predefined COA names. The partial ratio helps to perform substring matching. The token_set_ratio( ) attempts to rule out differences in the strings, calls ratio on three particular substring sets and returns the max. Additional validation may be performed by cross-referencing key features to ensure accurate identification. Furthermore, a rule may be implemented to align COA family hierarchies using the acronym pattern, full name pattern, and a combination of terms guided by experts.

Traditional methods for COA strategies struggle with variations in text, such as acronyms, hyphenation, or other formatting differences, which may overlook recent COA data, leading to poor COA strategies, resulting in failure to meet clinical endpoints. The present disclosure addresses these challenges by combining acronym matching with fuzzy string matching and additional data verification to ensure that the correct COA is identified. The disclosure comprises a text matching algorithm that identifies COA names in text data sources by leveraging acronym matching and fuzzy string matching. The process begins by extracting potential acronyms and the number of items from the text. The algorithm then matches these acronyms against an existing list of COA acronyms. If a match is found, further validation is performed by comparing the full COA name, therapeutic indications, and other associated features. If no acronym match is found, the algorithm resorts to fuzzy string matching of the full COA names against the text. Even with a high similarity score, additional features are checked to confirm the correct identification of the COA.

The algorithm may use a similarity threshold of 85%, as determined through empirical testing and human verification, to balance accuracy and recall. The results are categorized into several stages according to the similarity score. The initial two stages provide the most precise outcomes, with COAs determined by the matching method having complete reliability. The third stage offers 95% accuracy, while the fourth stage is divided into substages: 4*a*, which has 90% accuracy, and 4*b*, with 85% accuracy. A final stage is included to encompass any COAs that were not captured in previous stages.

Two algorithms have been developed and follow the logic described below:

A version of the algorithm

Stage 1: exact match with COA acronym

Extraction of all possible COA acronyms from CT.gov outcome text. Elimination of the duplicates to get one acronym per outcome (ISI).

For each distinct acronym, it looks at all the possible acronym matches in the PROQOLID list.

The acronym match is determined either at Stage 1*a*, 1*b* or 1*c*, depending on the acronym word count.

Stage 1*a*: exact match with COA acronym with word count=1

If the acronym is hyphenated (e.g., PHQ-9, GAD-7, SES-CD, etc.), and it is a 100% exact match: MATCH, the algorithm stops.

If the acronym is not hyphenated, it goes to the next step:

If the corresponding full name is found with 80% similarity in CT.gov outcome, it is a MATCH, the algorithm stops.

If not, if there is a 95% match between PROQOLID therapeutic indication either CT.gov conditions or MeSH term or outcome text, it is a MATCH.

If not, it goes to stage 2.

Stage 1*b*: exact match with COA acronym with word count=2

If it is 100% exact match with Acronym

If 80% of full name match is found: MATCH.

If not, if PROQOLID therapeutic indication 95% matches either CT.gov conditions or MeSH terms or outcome: MATCH.

If not, stage 2.

Stage 1*c*: exact match with COA acronym with word count >2

If >=90% match with the acronym: MATCH. This accounts for spelling differences.

If not, stage 2.

Stage 2: Exact match to COA full name.

It looks if there is any match between CT.gov outcome and COA full names from PROQOLID.

If there is 100% match with COA full name:

It further looks if there are any other COA full names in PROQOLID that contain similar words. Ex. "Crohn's Disease Activity Index", this sequence is also contained in the COA "Pediatric Crohn Disease Activity Index"

If there are no similar COA full names: MATCH.

If there are similar COA full names: it chooses one COA based on:

Number of items: if it finds back the corresponding number of items as a number in CT.gov outcome text: MATCH.

If not, additional words matched: if there is no match based on number of items, it looks for the words that differ between the similar COA names, and if these additional words are found within CT.gov outcome text: MATCH. Ex. if there is "pediatric" anywhere in the CT.gov outcome text "Pediatric Crohn Disease Activity Index".

Stage 3: 95% partial match to COA full name

Similar logic as in stage 2, but lowering the threshold of the fuzzy matching:

It looks if there is any 95% match between CT.gov outcome and COA full names from PROQOLID.

If there is 95% match with COA full name:

It further looks if there are any other COA full names in PROQOLID that contain similar words. Ex. "Quality of Life Inventory" also contained in the COA "Pediatric Quality of Life Inventory Infant Scales".

If there are no similar COA full names: it confirms the 95% match based on:

If number of items matches: MATCH

If not, if Therapeutic indication matches: MATCH

If either number of items or indication does not, it goes to stage 4.

If there are similar COA full names: it chooses one COA based on:

Number of items: MATCH.

If not, Additional words matched: MATCH (ex. "Pediatric" and "Infant Scales").

If not, Therapeutic indication: MATCH.

If not, it goes to stage 4*a*.

Stage 4*a:* 90% partial match to COA full name.

Lowering the threshold, with additional possibilities for selecting the correct match.

It looks if there is any 90% match between CT.gov outcome and COA full names from PROQOLID.

If there are any 90% matches with COA full name:

If number of items match: MATCH.

If not, if Therapeutic indication match: MATCH.

If not, if Author match: MATCH.

"If not, if the first word of the full name match: MATCH.

If not, stage 4*b*.

Stage 4*b:* 85% partial match to COA full name

Exact same procedure as stage 4*a* but lowering the threshold.

If 85% match with COA full name:

If number of items match: MATCH.

If not, if Therapeutic indication match: MATCH.

If not, if Author match: MATCH.

If not, if the first word of the full name match: MATCH.

If not, stage 5.

Stage 5: 70% math of the word order to any of COA full name

It looks for any of the words of PROQOLID COA full names, including the stop words, in CT.gov outcome.

If 70% of the order of words is found: MATCH.

Words do not have to be consecutive in the sentence.

V2 algorithm: The regular expression pattern may be updated to capture all possible patterns of the Acronym. The rule to map COA family hierarchies may be added based on the Acronym pattern, full name pattern and combination of words based on domain knowledge expertise.

In an embodiment, the final result after executing the rule-based algorithm may look like table 6 below:

TABLE 6

| NCT ID | MESH TERMS | CONDITIONS | Outcome_type | OUTCOME | Stage1_results | Stage2_results |
|---|---|---|---|---|---|---|
| NCT02129751 | Depressive Disorder Depression Depressive Disorder Major | Major Depressive Disorder | primary outcomes | Mean change from Baseline to EOt in total CDRS-R (raw) score \| Change from Baseline to EOt in total Children's Depression Rating Scale - Revised (CDRS-R). A higher score indicates a more profound state of depression. The interviewer rates 17 symptom areas; the symptom scores are summed to gererate a total score. The total score ranges from 17 to 108. | ["Children's Depression Rating Scale-Revised"] | [ ] |
| NCT02928094 | Angina Pectoris Myocardial Ischemia Coronary Artery Disease Angina Stable Ischemia | Angina Stable | secondary outcome | Change in quality of life \| Seattle Angina Questionnaire | [ ] | ['Seattle Angina Questionnaire'] |
| NCT03070132 | Trigeminal Neuralgia Neuralgia | Trigeminal Neuralgia | secondary outcomes | Change From Baseline in the Work Productivity and Activity Impairment (WPAI) Neuropathic Pain (V2.0) Score by Visit During the Long Term Extension (LTE) Period \| the WPAI questionnaire is a validated instrument to measure impairments in work and activites. The WPAI yields four types of scores: 1. Absenteeism (percentage of work time missed) 2. Presenteeism (percentage of impairment at work/reduced on-the-job effectiveness) 3. Work productivity loss (percentage of overall work impairment [absenteeism plus | [ ] | [ ] |

TABLE 6-continued

| | | | | | | |
|---|---|---|---|---|---|---|
| | | | | presenteeism]) 4. Activity Impairment (percentage of overall activity impairment). WPAI outcomes are expressed as impairment percentages, with higher numbers indicating greater impairment and less productivity. | | |
| NCT028111333 | Anxiety Disorders Bipolar Disorder | Bipolar Disorder Anxiety Disorders Anxiety | primary outcomes | To measure the safety of myo-inositol, anxiety and mood symptoms will be measured using the Patient Global Index of Change Severity (PGIC-S). ∣ This scale is a parent and child report tool that evaluates participants' anxiety and assesses if there has been a decline in clinical status Answer options are "0-None", "1-Mild", "2-Moderate", and "3-Severe" and describe symptoms of anxiety. Higher scores mean worse outcome. | [ ] | [ ] |
| NCT03070132 | Trigeminal Neuralgia Neuralgia | Trigeminal Neuralgia | secondary outcomes | Change From Baseline in the Penn Facial Pain Scale-Revised (PENN-FPS-R) Score by Visit During the Long Term Extension (LTE) Period ∣ The Penn-FPS-R is a new 12-item Health-Related Quality of life Outcome measure with content validity that can be used to assess and monitor the impact of Trigeminal Neuralgia and | ['Penn Facial Pain Scale-Revised'] | [ ] |

TABLE 6-continued

| | | | | | | |
|---|---|---|---|---|---|---|
| | | | | facial pain treatment interventions in both clincal practice and research. This scale uses the 0-10 numeric rating scale (NRS) to quantify the pain impact different activites and quality of life items, where 0 indicates no interference and 10 indicates complete interference. The sum of the rated NRS score will be calculated. | | |
| NCT03463954 | Neoplasms Breast Neoplasms | Malignant Neoplasm of Breast | secondary outcomes | Health-related quality of life outcome measures at three timepoint via EORTC QLQ-C30 & QLQ-BR23 questionnaire (baseline and 4-6 weeks post-laser ablation and post-surgery) \| Health-related quality of life outcome measures | ['EORTC Quality of Life Questionnaire-Core Questionnaire'] | [ ] |

| NCT ID | Stage3_results | Stage4_results | Stage4b_results | Stage5_results | Overall_Results | Acronym_matched |
|---|---|---|---|---|---|---|
| NCT02129751 | ['Session Rating Scale'] | [ ] | [ ] | [ ] | ["Children's Depression Rating Scale-Revised"] ['25806'] [ ][ ] ['Session Rating Scale'] ['393408'] [ ][ ][ ][ ][ ][ ] | ['CDRS-R'] |
| NCT02928094 | [ ] | [ ] | [ ] | [ ] | [ ][ ] ['Seattle Angina Questionnaire'] ['25288'][ ][ ] [ ][ ][ ][ ][ ] | [ ] |
| NCT03070132 | [ ] | ['Work Productivity and Activity Impairment: Lupus'] | [ ] | [ ] | [ ][ ][ ][ ][ ][ ] ['Work Productivity and Activity Impairment: Lupus'] ['54652'][ ][ ] [ ][ ] | [ ] |
| NCT028111333 | [ ] | [ ] | [ ] | ['Global Index of Safety'] | [ ][ ][ ][ ][ ] [ ][ ][ ][ ][ ] ['Global Index of | [ ] |

TABLE 6-continued

| | | | | | | |
|---|---|---|---|---|---|---|
| | | | | | Safety'] ['25119'] | |
| NCT03070132 | [ ] | [ ] | [ ] | [ ] | ['Penn Facial Pain Scale-Revised'] ['432642'] [ ][ ][ ][ ][ ] [ ][ ][ ][ ][ ] | ['PENN-FPS-R'] |
| NCT03463954 | [ ] | [ ] | [ ] | [ ] | ['EORTC Quality of Life Questionnaire-Core Questionnaire'] ['25256'] [ ][ ][ ][ ][ ] [ ][ ][ ][ ][ ] | ['EORTCQLQ-C30'] |

| NCT ID | Acronym_matched_Fullname | Acronym_partial_matched | Acronym_partial_matched_Fullname | Acronym_partial_testing | Items_collection | Acronym_collection | COA family |
|---|---|---|---|---|---|---|---|
| NCT02129751 | ["Children's Depression Rating Scale-Revised"] | [ ] | [ ] | [ ] | 0 | EOTCDRS-REOTCDRS-R | [ ] |
| NCT02928094 | [ ] | [ ] | [ ] | [ ] | 0 | | [ ] |
| NCT03070132 | [ ] | [ ] | [ ] | [ ] | 0 | WPAI LTE WPAI WPAI WPAI | ['WPAI'] |
| NCT028111333 | [ ] | [ ] | [ ] | [ ] | 0 | PGIC-S 0-None 1-Miled 2-Moderate 3-Severe | [ ] |
| NCT03070132 | ['Penn Facial Pain Scale-Revised'] | [ ] | [ ] | [ ] | 12 | Scale-Revised PENN-FPS-RLTE Penn-FPS 12-item Health-Related 0-10 NRS NRS | ['NRS'] |
| NCT03463954 | ['EORTC Quality of Life Questionnaire-Core Questionnaire'] | [ ] | [ ] | [ ] | 23 | EORTCQLQ-C30QLQ-BR234-6 Health-related | ['EORTC'; EORTC'] |

Structure of the Algorithm:

Topology: The topology may include rule-based logic combined with fuzzy matching techniques. The system may be structured as follows:

Input Layer: Take in text data and a set list of COA names and their features.

Acronym Matching Module: Identify acronyms within the text and check them against the COA acronym database.

Fuzzy Matching Module: Utilize fuzzy string matching algorithms from the Fuzz library to evaluate text against complete COA names.

Validation Module: Check extra features like therapeutic uses, item count, and author identities for match confirmation.

Output Layer: Deliver the most accurately matched COA name with a corresponding confidence level.

End Conditions: The process concludes when either a valid match is found, or all potential matches have been evaluated against the set threshold.

Technical Contribution and Technical Effect: The algorithm provides the following technical contributions:

Enhanced Accuracy: The combination of acronym matching, fuzzy string matching, and feature verification significantly improves the accuracy of text matching in noisy and unstructured datasets.

Robustness: The algorithm's capacity to deal with different text formats, abbreviations, and small typographical mistakes enhances the algorithm's robustness compared to traditional exact matching methods.

Empirical Validation: The algorithm has been tested with varying thresholds, and an optimal threshold of 85% has been determined to balance accuracy and recall. Empirical results show that the algorithm correctly identifies COA even when the text contains significant variations.

Mathematical Justification: The use of Levenshtein distance in fuzzy matching methods, combined with rule-based logic for acronym matching, provides a sound mathematical basis for the algorithm's performance.

Human Inputs

Model Structure: Business experts have established regulations for identifying acronyms and determining the criteria for similarity ratings. Additionally, protocols at various phases may ensure accurate detection of the COA. Moreover, a regulation may be introduced to organize COA family structures using patterns of acronyms, complete names, and a mix of terms, directed by the knowledge from business experts.

Algorithm Tuning: Both the technical and business experts have manually verified and adjusted the threshold levels based on the data to ensure highly precise identification of COA.

The system leverages a suite of Machine/Deep Learning algorithms for exploration of factors associated with assessment of COA and subsequently tracks clinical repositories and scientific publications with COAs. The system adopts and stacks numerous techniques for performing the tasks such as pre-processing, exploratory analysis and prediction of presence of COA. To get a predictive model which is independent from an event, either historic or current, the model extends to include datasets, and the form of the model takes on a temporal predictive nature, with minor corrections to be made as data feedback is fed back into the model as the assessment of COAs proceeds. The data used may reflect historical data-data that originated from events that were carried out or observed sometime in the past.

In an example, the factors that prove to be influential and predictive in nature to the tracking of a COA, over time, with AI carried out by the analytics communication device 116, and predictive communication device 118, get better in terms of predicting the model. The factors may change over time and the trends may change in terms of increasing issues that impinge on thresholds. The system 100 adapts as new information emerges, AI machine learning may ease the burden in terms of defining the models into the future and evolve to assist in selecting and identifying clinical trial data and publications data with high probability of occurrence of COA.

The system uses AI applications like Natural Language Processing (NLP) techniques that analyze unstructured data, such as medical literature and adverse event reports, to extract meaningful insights related to drug interactions, adverse effects, or patient outcomes. Machine Learning (ML) algorithms, including supervised learning classification algorithms, aid in categorizing COAs based on historical patterns and existing labelled data. This analysis helps in identifying potential risks by extracting meaningful insights from the data.

In an embodiment, the system may use AI-driven anomaly detection techniques such as machine learning algorithms like Isolation Forests or One-Class SVM that detect unusual data patterns or outliers that may indicate occurrence of COA. As an example, the classification of a publication is based on whether the occurrence of a COA is at or above the threshold level, and the data used to make the classification (prediction) consist of the remaining acquired data as a function of time. SVM may be trained to predict the presence of COA from the other coincident data, and/or may be trained to predict from the other data whether the probability of occurrence of COA will be higher in a similar publication in the future. By extrapolating the values of the other data into the future, it is also possible to use those extrapolated data to predict the future occurrence of COA, using an ensemble model that is trained with concurrent other data. Because the model analysis is repeated for all possible threshold levels of occurrence of COA, the analysis collectively endeavors to predict the current or future numerical value of occurrence of COA. The ML model may further utilize clustering techniques, where the machine learning algorithm is provided with unlabelled or unclassified data, which leaves the algorithm to identify hidden structures amongst the cases. SVM can be used by a user interface to perform SVM training, classification, and prediction, and to automatically capture and identify clusters and generate output to a user interface. The Classifier model may be a cross-platform user interface. In SVM clustering, the clustering can be further combined with k-means clustering to accelerate the training and prediction of the model. Predictive models developed using AI techniques help forecast deviations from expected data trends, enabling proactive COA tracking strategies.

In an embodiment, the AI model used for the tracking of COA from clinical trial repositories and scientific publications may be an Explainable artificial intelligence (XAI) model or Explainable AI model. Explainable AI may be used to describe an AI model that provides reasoning or justification for the decisions taken by the model thus allowing for transparency in the model. xAI algorithms are programmed to describe its purpose, rationale and decision-making process in a way that can be understood by the average person. Explainable AI may address certain issues pertaining to AI-based analysis such as bias, transparency, safety, and causality. Bias refers to potentially flawed AI resulting from biased training data. xAI is often discussed in relation to deep learning and plays an important role in the FAT ML model (fairness, accountability and transparency in machine learning). As the model provides insights into taking its decisions and making predictions, tracking of a COA by this model is better understood by the users of the model and the clinical trial sponsors. Explainable AI technique provides an effective manner of illustrating the back-end reasoning process of the AI system at a considerably granular level, which allows the user to make an informed decision or accept a decision made on behalf thereof. An ontology may be created and associated with the clinical trial data. Historical clinical trial data may be parsed frequently and curated to form ontologies a. Unsupervised learning, for example, k-means clustering, can be used to cluster feature vectors extracted from the entire data, which may be in the form of structured or unstructured data. The ontology is incrementally and continuously refined after the initial creation by the interaction of the AI system with the real world as new data becomes available. In addition, the curated data is also used for prediction of COA occurrence and determination of COA tracking strategy.

As the model allows for understanding the various features, the model may determine the keywords which need more weightage. The disclosure provides a consistent computable COA tracking based on a configurable system of weightings assigned to the keywords. Further, the model may determine the preference that may be given to certain training datasets, such as the domain specific determination of a COA, for predicting the occurrence of a COA in an outcome. This results in data explainability, which is understanding the data that is used as input and for training purposes, and how the end result of the model is predicted. In an embodiment, the model may allow the sponsors and researchers to interpret how it is arriving at the prediction of COA occurrence, and how that is used for the extraction of COA names. The model also provides for model explainability so that the user understands the model, how the end result is reached, thereby resulting in more acceptance of the model.

Data Enrichment and Model Refinement may be performed to expand the dataset and refine predictive models with new inputs. Environmental and behavioral data is integrated, and the model is configured for continuous Learning Mechanism. When combined into a single system, detection and prediction models create a synergistic effect that offers a comprehensive approach for determination of COA. This integrated system can simultaneously identify COA and predict future occurrence of COA. By leveraging the strengths of the models, a more effective and efficient COA tracking strategy may be implemented, enhancing determination, continuous monitoring, and overall management of extraction of COA names.

Figures 12A, 12B:
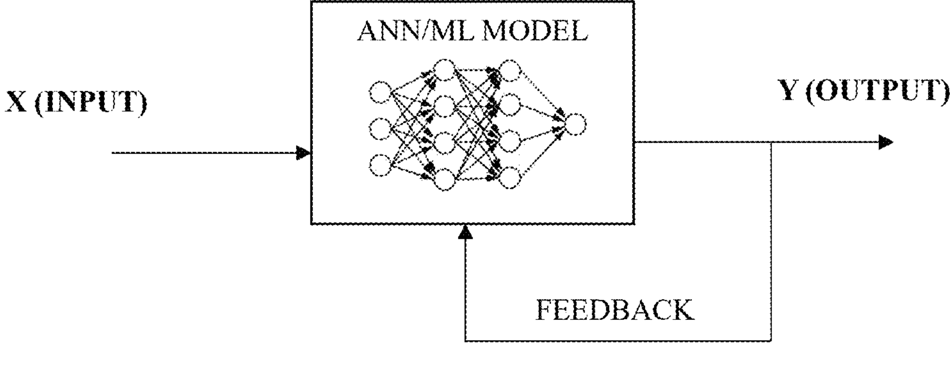
FIG. 12A shows a structure of the neural network/machine learning model with a feedback loop.
FIG. 12B shows a structure of the neural network/machine learning model with reinforcement learning.

FIG. 12A shows a structure of the neural network/machine learning model with a feedback loop. An Artificial neural networks (ANNs) model comprises an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed to the next layer of the network. A machine learning model or an ANN model may be trained on a set of data to take a request in the form of input data, make a prediction on that input data, and then provide a response. The input to the model may include data extracted from clinical repositories and scientific publications. The model may learn from the data. Learning can be supervised learning and/or unsupervised learning and may be based on different scenarios and with different datasets. Supervised learning comprises logic using at least one of a decision tree, logistic regression, and support vector machines. Unsupervised learning comprises logic using at least one of a k-means clustering, a hierarchical clustering, a hidden Markov model, and an apriori algorithm. The output layer may predict the occurrence of COA in the extracted data based on a predefined threshold value. In another embodiment, the data with the occurrence of COA may be used as input data and the output layer may predict and detect the COA names.

In an embodiment, ANN may be a Deep Neural Network (DNN), which is a multilayer tandem neural network comprising Artificial Neural Networks (ANN), Convolution Neural Networks (CNN) and Recurrent Neural Networks (RNN) that can recognize features from inputs, do an expert review, and perform actions that require predictions, creative thinking, and analytics. In an embodiment, ANNs may be Recurrent Neural Network (RNN), which is a type of Artificial Neural Networks (ANN), which uses sequential data or time series data. Deep learning algorithms are commonly used for ordinal or temporal problems, such as language translation, Natural Language Processing (NLP), speech recognition, and image recognition, etc. Like feedforward and convolutional neural networks (CNNs), recurrent neural networks utilize training data to learn. They are distinguished by their "memory" as they take information from prior input via a feedback loop to influence the current input and output. An output from the output layer in a neural network model is fed back to the machine learning model through the feedback. The variations of weights in the hidden layer(s) will be adjusted to fit the expected outputs better while training the model. This will allow the model to provide results with far fewer mistakes.

The neural network is featured with the feedback loop to adjust the system output dynamically as it learns from the new data. In machine learning, backpropagation and feedback loops are used to train an AI model and continuously improve it upon usage. As the incoming data that the model receives increases, there are more opportunities for the model to learn from the data. The feedback loops, or backpropagation algorithms, identify inconsistencies and feed the corrected information back into the model as an input.

Even though the AI/ML model is trained well, with large sets of labelled data and concepts, after a while, the models' performance may decline while adding new, unlabelled input due to many reasons which include, but not limited to, concept drift, recall precision degradation due to drifting away from true positives, and data drift over time. A feedback loop to the model keeps the AI results accurate and ensures that the model maintains its performance and improvement, even when new unlabelled data is assimilated. A feedback loop refers to the process by which an AI model's predicted output is reused to train new versions of the model. This is also used to make the model a self-learning model.

Initially, when the AI/ML model is trained, a few labelled samples comprising both positive and negative examples of the concepts (for e.g., the data extracted from clinical repositories and scientific publications) are used that are meant for the model to learn. Afterward, the model is tested using unlabelled data. By using, for example, deep learning and neural networks, the model can then make predictions on whether the desired concept/s (e.g., the occurrence of COA and extraction of COA names) are in unlabelled images. Each image is given a probability score where higher scores represent a higher level of confidence in the models' predictions. Where a model gives an image a high probability score, it is auto-labelled with the predicted concept. However, in the cases where the model returns a low probability score, this input may be sent to a controller (may be a human moderator) which verifies and, as necessary, corrects the result. The human moderator may be used only in exception cases. The feedback loop feeds labelled data, auto-labelled or controller-verified data back to the model dynamically and is used as training data so that the system can improve its predictions in real-time and dynamically.

FIG. 12B shows a structure of the neural network/machine learning model with reinforcement learning. The network receives feedback from authorized networked environments. Though the system is similar to supervised learning, the feedback obtained in this case is evaluative not instructive, which means there is no teacher as in supervised learning. After receiving the feedback, the network performs adjustments of the weights to get better predictions in the future. Machine learning techniques, like deep learning, allow models to take labelled training data and learn to recognize those concepts in subsequent data and images. The model may be fed with new data for testing, hence by feeding the model with data it has already predicted over, the training gets reinforced. If the machine learning model has a feedback loop, the learning is further reinforced with a reward for each true positive of the output of the system. Feedback loops ensure that AI results do not stagnate. By incorporating a feedback loop, the model output keeps improving dynamically and over usage/time. This also results in making the model a self-learning model.

Figure 13:
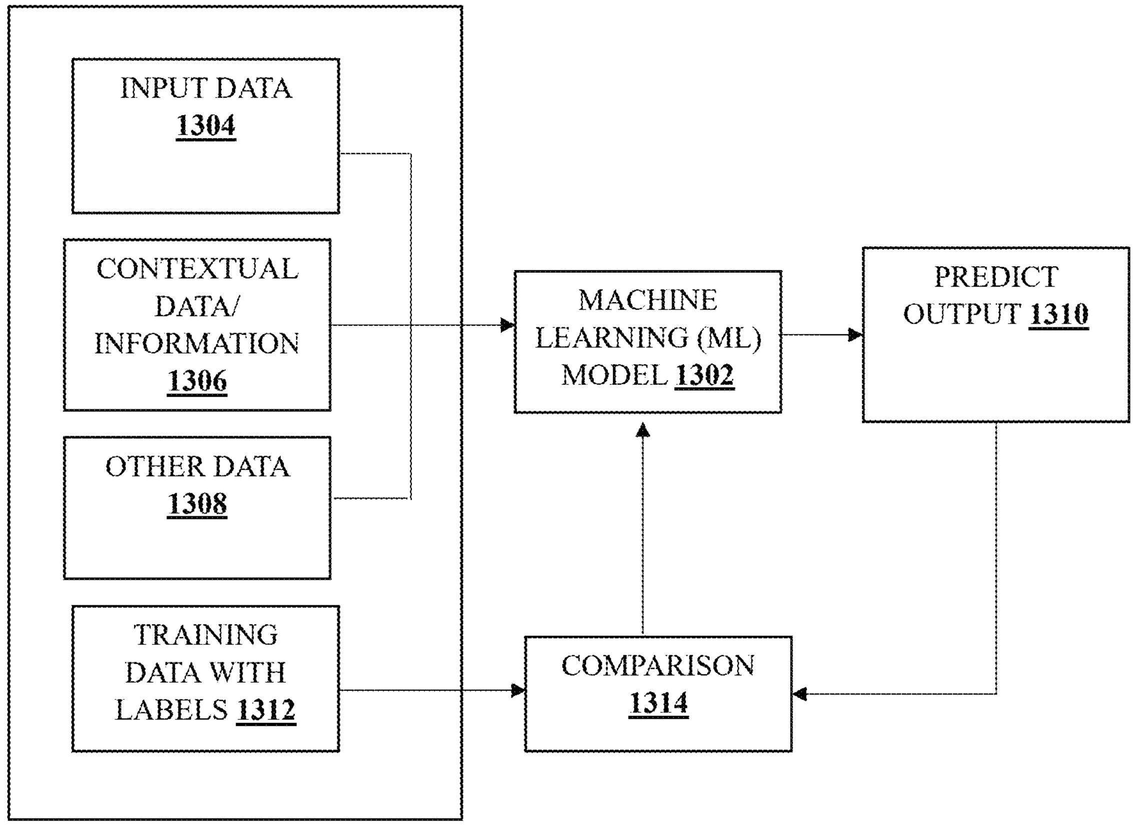
FIG. 13 illustrates an example block diagram for an Artificial Intelligence and Machine Learning (AI/ML) model used in a system according to an embodiment.

FIG. 13 illustrates an example block diagram for an Artificial Intelligence and Machine Learning (AI/ML) model used in a system according to an embodiment.

Referring to FIG. 13, the machine learning model 1302 may take as input clinical repository data and/or scientific publication data 1304, contextual data/information 1306, and any other data 1308 and learn to identify from the available data, an optimized method to extract COA names. The aforementioned types of data may correlate with the prediction of occurrence of COA, and such correlation may be automatically learned by the machine learning model 1302. The contextual data/information 1306 may include historical data that may affect the tracking of COA in clinical repositories data. Training data with labels 1312 may comprise, for example, historical data with occurrence of COA. The systems and methods of the present disclosure may also provide data analytics information that may be used later to improve the prediction accuracy of tracking and occurrence of COA. Prediction or predictive analysis uses probability based on the data analysis and processing.

In an embodiment, during training, machine learning model 1302 may process the training data sample (e.g., clinical repository data 1304, contextual data/information 1306, and any other data 1308), and, based on the current parameters of machine learning model 1302, predict output 1310 which may be an optimized method to track a COA. In an embodiment, the real-time data may be processed using one or more machine learning models 1302, trained and based on similar types of data to correctly track COAs. The model may be tested periodically at different intervals of time, such as when new training data is added, or when the new training data is different from the training data. In an embodiment, during training, the output 1310 and the training data with labels 1312 may be compared at 1314. For example, comparison 1314 may be based on a loss function that measures a difference between the predicted/detected output and training data with labels 1312. Based on the comparison 1314 or the corresponding output of the loss function, a training algorithm may update the parameters of machine learning model 1302 with the objective of minimizing the differences or loss between subsequent predicted output 1310 and corresponding labels 1312. By iteratively training in this manner, machine learning model 1302 may "learn" from the different training data samples and become better at predicting output 1310. In an embodiment, machine learning model 1302 is trained using data which is specific to a function for which the model is used for predicting adjustments to the settings to provide accurate estimation of occurrence of COA. In an embodiment, machine learning model 1302 is trained using data which is general to the different functions and is used for predicting adjustments for prediction of the estimation of occurrence of COA. In an embodiment, the device information may be given weights and provided as an input to the AI/ML system.

Using the training data, a machine learning model 1302 may be trained so that it recognizes features of pre-processed input data that signify or correlate to certain event types. For example, a trained machine learning model 1302 may recognize data features that signify the likelihood of occurrence of COA, as an actionable event. In an embodiment, the features may have meaningful interpretations, such as occurrence of COA. In an embodiment, the events that change the probability of occurrence of COA are used as training data or pre-processed input data for training. The features result in improvement of the model. The features may also be unintelligible to humans and may simply represent data patterns that tend to be present when certain event types occur. Through training, machine learning model 1302 may learn to identify predictive and non-predictive features and apply the appropriate weights to the features to optimize predictive accuracy of machine learning model 1302. In embodiments where supervised learning is used and each training data sample has a label, the training algorithm may iteratively process each training data sample and generate a predicted output 1310. Based on the comparison results at 1314, the training algorithm may adjust the parameters/configurations (e.g., weights) of the model 1302, accordingly, to minimize the differences between the generated predicted output 1310 and the corresponding labels 1312. In an embodiment, the model is a self-learning model built based on the learning, the training, and the feedback received from the data and environment. Any suitable machine learning model and training algorithm may be used, including, e.g., decision trees, clustering algorithms, neural networks, and any other suitable machine learning techniques. Once trained, machine learning model 1302 may take pre-processed input data and detect the objects along with their corresponding confidence score. In an embodiment, machine learning model 1302 is an artificial neural networks (ANN) model.

In an embodiment, the machine learning model is configured to learn using labelled data using a supervised learning method, wherein the supervised learning method comprises logic using at least one of a decision tree, a logistic regression, a support vector machine, a k-nearest neighbors, a Naïve Bayes, a random forest, a linear regression, a polynomial regression, and a support vector machine for regression.

In some embodiments, the machine learning model is configured to learn from a real-time data using an unsupervised learning method, wherein the unsupervised learning method comprises logic using at least one of a k-means clustering, a hierarchical clustering, a hidden Markov model, and an apriori algorithm.

In some embodiments, the machine learning model has a feedback loop, wherein an output from a previous step is fed back to the machine learning model in real-time to improve the performance and accuracy of the output of a next step.

In some embodiments, the machine learning model has a feedback loop, wherein the learning is further reinforced with a reward for each true positive of the output of the system.

Figure 14A:
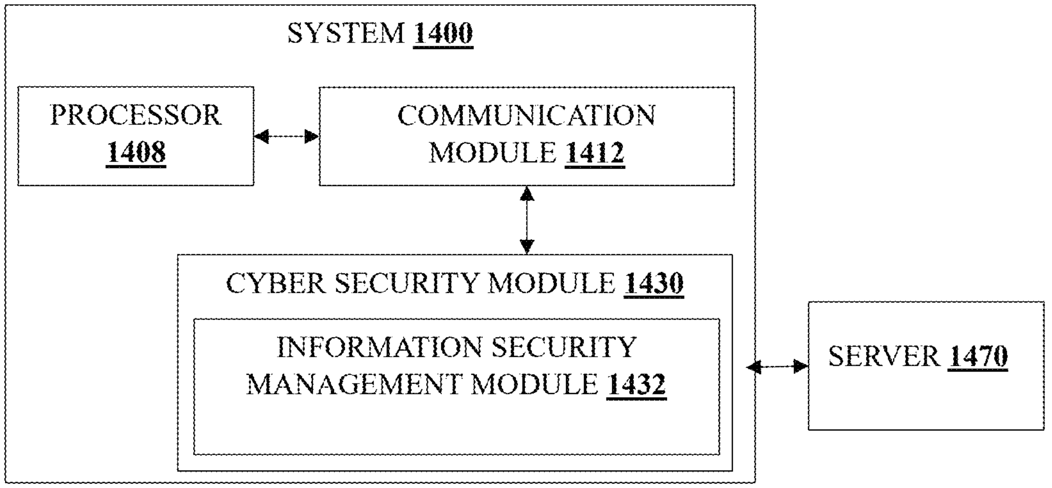
FIG. 14A shows a block diagram of the cyber security module in view of the system and server.

FIG. 14A illustrates the block diagram of the cyber security module in view of the system and server according to an embodiment.

In one aspect, a secure communication management (SCM) computer device for providing secure data connections is provided. The SCM computer device includes a processor in communication with memory. The processor is programmed to receive, from a first device, a first data message. The first data message is in a standardized data format. The processor is also programmed to analyze the first data message for potential cyber security threats.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

Referring to FIG. 14A, system 1400 comprising processor 1408, communication module 1412, cyber security module 1430, and information security management module 1432 in communication with server 1470, is shown. The communication of data from the processor 102, shown in FIG. 1, of the system 100 and the server 1470, shown in FIG. 14A, through the communication module 1412 is first verified by the information security management module 1432 before being transmitted from the system to the server or from the server to the system. The information security management module is operable to analyze the data for potential cyber security threats, to encrypt the data when no cyber security threat is detected, and to transmit the data encrypted to the system or the server. In an embodiment, the communication of data from the processor 102 to the server 112 in FIG. 1, may be the data that is communicated by the communication module 1412 to the server 1470. The communication of data from the processor 102 to the database 108, the analytics communication device 116, and the predictive communication device 118 in FIG. 1, may be first verified by the information security management module 1432 of the cyber security module 1430 to ensure integrity of data. Once the data is sourced from clinical repositories and scientific publications, for that data to accurately help determine the occurrence of COA, it may be kept from unauthorized access by verification provided by the cyber security module 1430. In an embodiment, the data sourced from clinical trial repositories and scientific publications may also be verified by the cyber security module to ensure that the data has not been tampered with. Further, as clinical trials data include data relating to participants and patients, to ensure that the data is not compromised, the privacy and security of data may be protected by verifying the data by the cyber security module 1430.

Figure 14B:
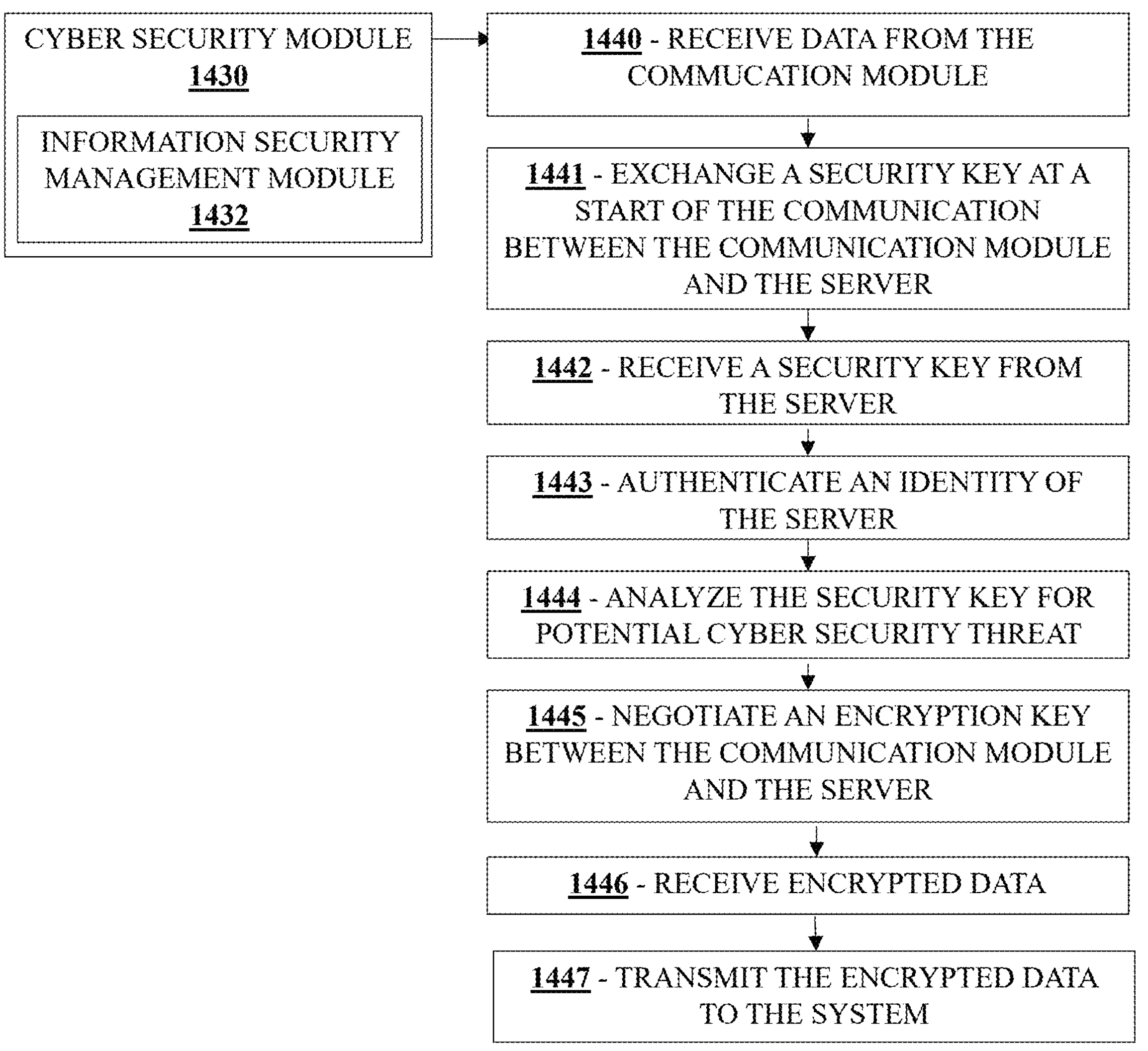
FIG. 14B shows an embodiment of the cyber security module.

FIG. 14B shows an embodiment of the cyber security module, in accordance with some embodiments of the present disclosure.

In an embodiment, the cyber security module further comprises an information security management module providing isolation between the system and the server. FIG. 14B shows the flowchart of securing the data through the cyber security module 1430. At step 1440, the information security management module is operable to receive data from the communication module. At step 1441, the information security management module exchanges a security key at a start of the communication between the communication module and the server. At step 1442, the information security management module receives a security key from the server. At step 1443, the information security management module authenticates an identity of the server by verifying the security key. At step 1444, the information security management module analyzes the security key for potential cyber security threats. At step 1445, the information security management module negotiates an encryption key between the communication module and the server. At step 1446, the information security management module receives the encrypted data. At step 1447, the information security management module transmits the encrypted data to the server when no cyber security threat is detected.

Figure 14C:
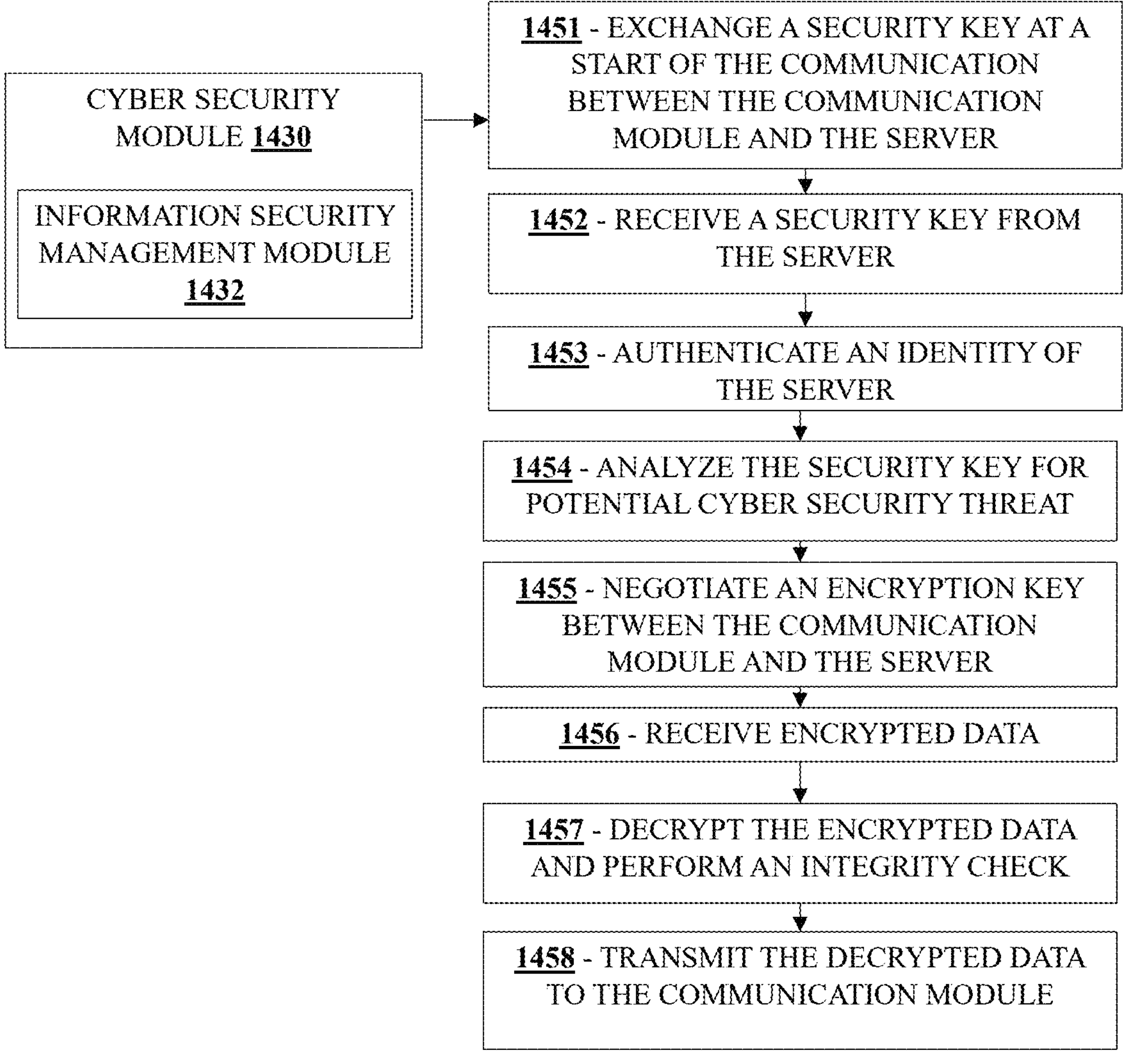
FIG. 14C shows another embodiment of the cyber security module.

In an embodiment, FIG. 14C shows the flowchart of securing the data through the cyber security module 1430. At step 1451, the information security management module is operable to: exchange a security key at a start of the communication between the communication module and the server. At step 1452, the information security management module receives a security key from the server. At step 1453, the information security management module authenticates an identity of the server by verifying the security key. At step 1454, the information security management module analyzes the security key for potential cyber security threats. At step 1455, the information security management module negotiates an encryption key between the communication module and the server. At step 1456, the information security management module receives encrypted data. At step 1457, the information security management module decrypts the encrypted data, and performs an integrity check of the decrypted data. At step 1458, the information security management module transmits the decrypted data to the communication module when no cyber security threat is detected.

In an embodiment, the integrity check is a hash-signature verification using a Secure Hash Algorithm 256 (SHA256) or a similar method.

In an embodiment, the information security management module is configured to perform asynchronous authentication and validation of the communication between the communication module and the server.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the decrypted data by checking accuracy, consistency, and any possible data loss during the communication through the communication module.

In an embodiment, the server is physically isolated from the system through the information security management module. When the system communicates with the server as shown in FIG. 14A, identity authentication is first carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed.

Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed. Signing identity comprises a public and a private key pair. In other words, signing identity is referred to as the common name of the certificates which are installed in the user's machine.

In an embodiment, both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting a Rivest-Shamir-Adleman (RSA) encryption algorithm. RSA is a public key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, the integrity check calculation is carried out on the data, the calculated Message Authentication Code (MAC) value is added with the header of the value data message, then the data (including the MAC of the header) is encrypted by using a 3DES algorithm, the header information of a security layer is added after the data is encrypted, and then the data is sent to the next layer for processing. In an embodiment the next layer refers to a transport layer in the Transmission Control Protocol/Internet Protocol (TCP/IP) model.

The information security management module ensures the safety, reliability, and confidentiality of the communication between the system and the server through the identity authentication when the communication between the two communication parties starts the data encryption and the data integrity authentication. The method is particularly suitable for an embedded platform which has less resources and is not connected with a Public Key Infrastructure (PKI) system and can ensure that the safety of the data on the server cannot be compromised by a hacker attack under the condition of the Internet by ensuring the safety and reliability of the communication between the system and the server.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

INCORPORATION BY REFERENCE

All references, including granted patents and patent application publications, referred herein are incorporated herein by reference in their entirety:

U.S. Pat. No. 11,621,085B1 titled "Computer network architecture with machine learning and artificial intelligence and active updates of outcomes";

US20210295956A1 titled "Systems and Methods for Hashing-Based Assessment of Electronic Clinical Trial Outcomes".

What is claimed is:

1. A system comprising:

a first machine learning model that comprises an ensemble model of a plurality of machine learning classifiers, wherein each the plurality of machine learning classifiers is independently trained to make one or more predictions and a final output is determined based on a hard voting algorithm applied to the one or more predictions of the plurality of machine learning classifiers, wherein the ensemble model is an integrated classifier model combining the plurality of machine learning classifiers, having diverse inductive biases and diverse learning mechanisms, wherein each of the plurality of machine learning classifiers is hyperparameter tuned to optimize performance of the ensemble model of the plurality of machine learning classifiers;

a processor storing instructions in a non-transitory memory that, when executed, cause the processor to:

acquire input data from one or more data sources;

pre-process the input data by removing noise and data inconsistencies from the input data to generate cleaned data;

splitting the cleaned data into one or more tokens;

assigning at least one Part-of-Speech (POS) tag to the one or more tokens to generate one or more tagged tokens;

applying lemmatization and performing Unicode normalization to the one or more tagged tokens to generate text data;

performing vectorization to convert the text data into feature vectors; and performing feature extraction and feature selection on the feature vectors to select relevant features of a first training dataset and a first validation dataset, wherein the first training dataset and the first validation dataset are distinct and different, wherein the independent training of each of the plurality of machine learning classifiers of the first machine learning model is performed using the relevant features of the first training dataset; and validate the first machine learning model using the relevant features of the first validation dataset.

2. The system of claim 1, wherein the input data comprises at least one of structured data, semi-structured data, and unstructured data.

3. The system of claim 1, wherein the system further comprises a second machine learning model.

4. The system of claim 3, wherein the processor is configured to pre-process actual data;

feed the pre-processed actual data to the ensemble model of the plurality of machine learning classifiers to classify one or more data points of the pre-processed actual data as one of a relevant data point and an irrelevant data point based on a predefined threshold value;

retrieve, using the first machine learning model, raw input data that corresponds to the one or more data points that are classified as the relevant data point, wherein the raw input data is the input data acquired from the one or more data sources; and feed retrieved raw input data of outcomes from the first machine learning model as an input to the second machine learning model.

5. The system of claim 4, wherein the input data is pre-processed by performing one or more preprocessing techniques using Term Frequency-Inverse Document Frequency (TF-IDF).

6. The system of claim 4, wherein the predefined threshold value is initially set based on at least one of outcomes of historical input data and predicted by the first machine learning model.

7. The system of claim 4, wherein the processor is further configured to:

train the second machine learning model using a second training dataset; and validate the second machine learning model using a second validation dataset.

8. The system of claim 7, wherein the second machine learning model is a self-learning model comprising a feedback layer that enables the second machine learning model to learn continuously from the retrieved raw input data.

9. The system of claim 7, wherein the processor is configured to extract, using the second machine learning model, one or more clinical outcome assessment names from the retrieved raw input data that are classified as relevant based on training provided to the second machine learning model.

10. The system of claim 7, wherein the processor is further configured to generate an output comprising harmonized clinical outcome assessment names.

11. The system of claim 3, wherein the second machine learning model is a Large Language model (LLM).

12. The system of claim 1, wherein the system is further configured to:

customize the ensemble model of the plurality of machine learning classifiers by performing manipulating the pre-processed input data to generate modified input data, adding, modifying, or removing at least one node of the ensemble model of the plurality of machine learning classifiers, and training the ensemble model of the plurality of machine learning classifiers using the modified input data.

13. The system of claim 1, wherein the plurality of machine learning classifiers comprises two or more of a Random Forest classifier model, an XGBoost model, a Support Vector Machine (SVM) model, a Stochastic Gradient Descent model, and a Logistic Regression model.

14. The system of claim 1, wherein the hard voting algorithm analyzes the one or more predictions from the plurality of machine learning classifiers and assigns a final class label based on a class predicted by a majority of the classifiers.

15. The system of claim 1, wherein the system is configured for tracking of a clinical outcome assessment.

16. The system of claim 1, wherein the first machine learning model is calibrated, selected, and ensembled from the plurality of machine learning classifiers evaluated against a set of performance criteria for tracking a clinical outcome assessment.

17. The system of claim 1, wherein the first machine learning model has a feedback loop, wherein an output from a previous step is fed back to the model in real-time to improve performance and accuracy of the output of a next step.

18. A method comprising:

acquiring input data from one or more data sources;

pre-processing the input data by removing noise and data inconsistencies from the input data to generate cleaned data;

splitting the cleaned data into one or more tokens;

assigning at least one Part-of-Speech (POS) tag to the one or more tokens to generate one or more tagged tokens;

applying lemmatization and performing Unicode normalization to the one or more tagged tokens to generate text data;

performing vectorization to convert the text data into feature vectors; and performing feature extraction and feature selection on the feature vectors to select relevant features of a first training dataset and a first validation dataset, wherein the first training dataset and the first validation dataset are distinct and different;

training independently each machine learning classifier of a plurality of machine learning classifiers of a first machine learning model, wherein the first machine learning model comprises an ensemble model of the plurality of machine learning classifiers, wherein each of the plurality of machine learning classifiers is independently trained to make one or more predictions and a final output is determined based on a hard voting algorithm applied to the one or more predictions of the plurality of machine learning classifiers, wherein the ensemble model is an integrated classifier model combining the plurality of machine learning classifiers, having diverse inductive biases and diverse learning mechanisms, wherein the independent training of each of the plurality of machine learning classifiers of the first machine learning model is performed using the relevant features of the first training dataset, wherein each of the plurality of machine learning classifiers is hyperparameter tuned to optimize performance of the ensemble model of the plurality of machine learning classifiers; and validating the first machine learning model using the relevant features of the first validation dataset.

19. A non-transitory computer-readable medium having stored thereon instructions executable by a computer system to perform operations comprising:

acquiring input data from one or more data sources;

pre-processing the input data by removing noise and data inconsistencies from the input data to generate cleaned data;

splitting the cleaned data into one or more tokens;

assigning at least one Part-of-Speech (POS) tag to the one or more tokens to generate one or more tagged tokens;

applying lemmatization and performing Unicode normalization to the one or more tagged tokens to generate text data;

performing vectorization to convert the text data into feature vectors; and performing feature extraction and feature selection on the feature vectors to select relevant features of a first training dataset and a first validation dataset, wherein the first training dataset and the first validation dataset are distinct and different;

training independently each machine learning classifier of a plurality of machine learning classifiers of a first machine learning model, wherein the first machine learning model comprises an ensemble model of the plurality of machine learning classifiers, wherein each of the plurality of machine learning classifiers is independently trained to make one or more predictions and a final output is determined based on a hard voting algorithm applied to the one or more predictions of the plurality of machine learning classifiers, wherein the ensemble model is an integrated classifier model combining the plurality of machine learning classifiers, having diverse inductive biases and diverse learning mechanisms, wherein the independent training of each of the plurality of machine learning classifiers is performed using the relevant features of the first training dataset, wherein each of the plurality of machine learning classifiers is hyperparameter tuned to optimize performance of the ensemble model of the plurality of machine learning classifiers; and validating the first machine learning model using the relevant features of the first validation dataset.

* * * * *